(12) United States Patent
Hughes

(10) Patent No.: US 8,673,341 B2
(45) Date of Patent: *Mar. 18, 2014

(54) INTRAOCULAR PRESSURE REDUCTION WITH INTRACAMERAL BIMATOPROST IMPLANTS

(75) Inventor: Patrick M. Hughes, Aliso Viejo, CA (US)

(73) Assignee: Allergan, Inc., Irvine, CA (US)

( * ) Notice: Subject to any disclaimer, the term of this patent is extended or adjusted under 35 U.S.C. 154(b) by 295 days.

This patent is subject to a terminal disclaimer.

(21) Appl. No.: 12/761,765

(22) Filed: Apr. 16, 2010

(65) Prior Publication Data

US 2010/0278898 A1 Nov. 4, 2010

Related U.S. Application Data

(63) Continuation-in-part of application No. 10/837,260, filed on Apr. 30, 2004, now Pat. No. 7,799,336.

(51) Int. Cl.
A61F 2/14 (2006.01)

(52) U.S. Cl.
USPC .......................................................... 424/428

(58) Field of Classification Search
None
See application file for complete search history.

(56) References Cited

U.S. PATENT DOCUMENTS

| | | | |
|---|---|---|---|
| 3,396,081 A | 8/1968 | Billek | |
| 3,749,776 A | 7/1973 | Eakins | |
| 3,845,770 A | 11/1974 | Theeuwes et al. | |
| 3,916,899 A | 11/1975 | Theeuwes et al. | |
| 4,008,864 A | 2/1977 | Torphammar et al. | |
| 4,014,335 A | 3/1977 | Arnold | |
| 4,052,505 A | 10/1977 | Higuchi | |
| 4,057,619 A | 11/1977 | Higuchi et al. | |
| 4,063,064 A | 12/1977 | Saunders et al. | |
| 4,088,864 A | 5/1978 | Theeuwes et al. | |
| 4,144,317 A | 3/1979 | Higuchi | |
| 4,158,005 A | 6/1979 | Bodor et al. | |
| 4,186,184 A | 1/1980 | Zaffaroni | |

(Continued)

FOREIGN PATENT DOCUMENTS

| | | |
|---|---|---|
| CA | 1333770 A1 | 1/1995 |
| EP | 0251680 | 1/1988 |

(Continued)

OTHER PUBLICATIONS

Allergan, 2005, Alphagan Product Information, Product Sheet, 0, 1-10.

(Continued)

*Primary Examiner* — Carlos Azpuru
(74) *Attorney, Agent, or Firm* — Louis V. Wollenberger; Joel B. German; Debra D. Condino

(57) ABSTRACT

The present invention provides a method of treating an ocular condition in an eye of a patient, comprising the step of placing a biodegradable intraocular implant in an eye of the patient, the implant comprising a prostamide and a biodegradable polymer matrix that releases drug at a rate effective to sustain release of an amount of the prostamide from the implant to provide an amount of the prostamide effective to prevent or reduce a symptom of an ocular condition of the eye, wherein said ocular condition is elevated IOP and said implant is placed in an intracameral location to dilate the outflow channels of the eye emanating from Schlemm's Canal.

5 Claims, 11 Drawing Sheets

(56) References Cited

U.S. PATENT DOCUMENTS

| | | | |
|---|---|---|---|
| 4,190,642 | A | 2/1980 | Gale et al. |
| 4,200,098 | A | 4/1980 | Ayer et al. |
| 4,281,654 | A | 8/1981 | Shell et al. |
| 4,285,957 | A | 8/1981 | Ayer et al. |
| 4,303,637 | A | 12/1981 | Shell et al. |
| 4,304,765 | A | 12/1981 | Shell et al. |
| 4,327,725 | A | 5/1982 | Cortese |
| 4,396,625 | A | 8/1983 | Yamamori et al. |
| 4,425,346 | A | 1/1984 | Horlington et al. |
| 4,454,151 | A | 6/1984 | Waterbury |
| 4,474,451 | A | 10/1984 | Mizokami et al. |
| 4,478,818 | A | 10/1984 | Shell et al. |
| 4,494,274 | A | 1/1985 | Thurlow |
| 4,521,210 | A | 6/1985 | Wong |
| 4,599,353 | A | 7/1986 | Bito |
| 4,649,151 | A | 3/1987 | Dougherty et al. |
| 4,656,186 | A | 4/1987 | Bommer et al. |
| 4,668,506 | A | 5/1987 | Bawa |
| 4,675,338 | A | 6/1987 | Bommer et al. |
| 4,693,885 | A | 9/1987 | Bommer et al. |
| 4,712,500 | A | 12/1987 | Montandon et al. |
| 4,853,224 | A | 8/1989 | Wong |
| 4,863,457 | A | 9/1989 | Lee |
| 4,865,846 | A | 9/1989 | Kaufman |
| 4,866,168 | A | 9/1989 | Dougherty et al. |
| 4,932,934 | A | 6/1990 | Dougherty et al. |
| 4,932,984 | A | 6/1990 | Nankee |
| 4,935,498 | A | 6/1990 | Sessler et al. |
| 4,959,217 | A | 9/1990 | Sanders et al. |
| 4,968,715 | A | 11/1990 | Dougherty et al. |
| 4,981,871 | A | 1/1991 | Abelson |
| 4,997,652 | A | 3/1991 | Wong |
| 5,002,962 | A | 3/1991 | Pandey et al. |
| 5,017,579 | A | 5/1991 | Gubin et al. |
| 5,019,400 | A | 5/1991 | Gombotz et al. |
| 5,028,621 | A | 7/1991 | Dougherty et al. |
| 5,028,624 | A | 7/1991 | Chan et al. |
| 5,034,413 | A | 7/1991 | Chan |
| 5,075,115 | A | 12/1991 | Brine |
| 5,089,509 | A | 2/1992 | Chandraratna |
| 5,093,349 | A | 3/1992 | Pandey et al. |
| 5,100,431 | A | 3/1992 | Buster et al. |
| 5,164,188 | A | 11/1992 | Wong |
| 5,166,331 | A | 11/1992 | Della Valle |
| 5,169,638 | A | 12/1992 | Dennis et al. |
| 5,171,741 | A | 12/1992 | Dougherty |
| 5,173,504 | A | 12/1992 | Dougherty |
| 5,190,966 | A | 3/1993 | Dougherty et al. |
| 5,198,460 | A | 3/1993 | Pandey et al. |
| 5,268,178 | A | 12/1993 | Calhoun et al. |
| 5,300,114 | A | 4/1994 | Gwon et al. |
| 5,314,905 | A | 5/1994 | Pandey et al. |
| 5,356,629 | A | 10/1994 | Sander et al. |
| 5,378,475 | A | 1/1995 | Smith et al. |
| 5,384,333 | A | 1/1995 | Davis et al. |
| 5,385,887 | A | 1/1995 | Yim et al. |
| 5,438,071 | A | 8/1995 | Clauss et al. |
| 5,443,505 | A | 8/1995 | Wong et al. |
| 5,459,159 | A | 10/1995 | Pandey et al. |
| 5,466,233 | A | 11/1995 | Weiner et al. |
| 5,501,856 | A | 3/1996 | Ohtori et al. |
| 5,504,074 | A | 4/1996 | D'Amato et al. |
| 5,516,522 | A | 5/1996 | Gholam et al. |
| 5,585,401 | A | 12/1996 | Brandt et al. |
| 5,587,371 | A | 12/1996 | Sessler et al. |
| 5,587,479 | A | 12/1996 | Makovec et al. |
| 5,597,897 | A | 1/1997 | Ron et al. |
| 5,655,832 | A | 8/1997 | Pelka et al. |
| 5,656,297 | A | 8/1997 | Bernstein et al. |
| 5,688,819 | A | 11/1997 | Woodward |
| 5,707,643 | A | 1/1998 | Ogura |
| 5,716,981 | A | 2/1998 | Hunter et al. |
| 5,766,242 | A | 6/1998 | Wong et al. |
| 5,770,589 | A | 6/1998 | Billson et al. |
| 5,776,699 | A | 7/1998 | Klein et al. |
| 5,798,349 | A | 8/1998 | Levy et al. |
| 5,824,072 | A | 10/1998 | Wong |
| 5,824,074 | A | 10/1998 | Koch et al. |
| 5,869,079 | A | 2/1999 | Wong |
| 5,877,207 | A | 3/1999 | Klein et al. |
| 5,882,682 | A | 3/1999 | Rork et al. |
| 5,906,920 | A | 5/1999 | Evans et al. |
| 5,913,884 | A | 6/1999 | Trauner et al. |
| 5,919,970 | A | 7/1999 | Song et al. |
| 5,922,773 | A | 7/1999 | Lipton et al. |
| 5,958,954 | A | 9/1999 | Klein et al. |
| 5,965,152 | A | 10/1999 | Galin |
| 5,972,326 | A | 10/1999 | Galin |
| 6,051,576 | A | 4/2000 | Ashton et al. |
| 6,066,675 | A | 5/2000 | Wen et al. |
| 6,074,661 | A | 6/2000 | Olejnik et al. |
| 6,217,869 | B1 | 4/2001 | Meyer et al. |
| 6,217,895 | B1 | 4/2001 | Guo et al. |
| 6,225,303 | B1 | 5/2001 | Miller et al. |
| 6,258,319 | B1 | 7/2001 | Hearst et al. |
| 6,270,492 | B1 | 8/2001 | Sinofsky |
| 6,270,749 | B1 | 8/2001 | Blumenkranz et al. |
| 6,271,220 | B1 | 8/2001 | Garst et al. |
| 6,274,614 | B1 | 8/2001 | Richter et al. |
| 6,290,713 | B1 | 9/2001 | Russell |
| 6,294,361 | B1 | 9/2001 | Horowitz et al. |
| 6,306,426 | B1 | 10/2001 | Olejnik et al. |
| 6,309,669 | B1 | 10/2001 | Setterstrom et al. |
| 6,317,616 | B1 | 11/2001 | Glossop |
| 6,319,273 | B1 | 11/2001 | Chen et al. |
| 6,331,313 | B1 | 12/2001 | Wong et al. |
| 6,357,568 | B1 | 3/2002 | Chen |
| 6,369,116 | B1 | 4/2002 | Wong et al. |
| 6,395,787 | B1 | 5/2002 | Woodward |
| 6,403,649 | B1 | 6/2002 | Woodward |
| 6,455,062 | B1 | 9/2002 | Olejnik |
| 6,482,854 | B1 | 11/2002 | Lipton et al. |
| 6,497,729 | B1 | 12/2002 | Moussy et al. |
| 6,537,568 | B2 | 3/2003 | Olejnik et al. |
| 6,548,078 | B2 | 4/2003 | Guo et al. |
| 6,565,871 | B2 | 5/2003 | Roser et al. |
| 6,573,280 | B2 | 6/2003 | Dreyer |
| 6,595,945 | B2 | 7/2003 | Brown |
| 6,699,493 | B2 | 3/2004 | Wong |
| 6,713,081 | B2 | 3/2004 | Robinson et al. |
| 6,728,918 | B1 | 4/2004 | Wong |
| 6,765,012 | B2 | 7/2004 | Andrews et al. |
| 6,899,717 | B2 | 5/2005 | Lathrop et al. |
| 7,589,057 | B2 | 9/2009 | Chang et al. |
| 7,592,364 | B2 | 9/2009 | Old et al. |
| 7,771,742 | B2 | 8/2010 | Hughes et al. |
| 7,799,336 | B2 | 9/2010 | Hughes et al. |
| 7,993,634 | B2 * | 8/2011 | Hughes et al. ............. 424/78.04 |
| 8,147,865 | B2 | 4/2012 | Huang et al. |
| 8,206,736 | B2 | 6/2012 | Hughes |
| 8,206,737 | B2 | 6/2012 | Hughes |
| 8,445,027 | B2 | 5/2013 | Hughes et al. |
| 2001/0023363 | A1 | 9/2001 | Harth |
| 2002/0032201 | A1 | 3/2002 | Olejnik et al. |
| 2002/0035264 | A1 | 3/2002 | Kararli et al. |
| 2002/0040015 | A1 | 4/2002 | Miller et al. |
| 2002/0094998 | A1 | 7/2002 | Burke et al. |
| 2002/0103255 | A1 | 8/2002 | Hellberg et al. |
| 2003/0018078 | A1 | 1/2003 | Woodward et al. |
| 2003/0069286 | A1 | 4/2003 | Chen et al. |
| 2003/0069560 | A1 | 4/2003 | Adamis et al. |
| 2003/0095995 | A1 | 5/2003 | Wong et al. |
| 2003/0185873 | A1 | 10/2003 | Chasin et al. |
| 2003/0199478 | A1 | 10/2003 | Andrews et al. |
| 2003/0220376 | A1 | 11/2003 | Masferrer |
| 2003/0225152 | A1 | 12/2003 | Andrews et al. |
| 2004/0054374 | A1 | 3/2004 | Weber |
| 2004/0058313 | A1 | 3/2004 | Abreu |
| 2004/0127843 | A1 | 7/2004 | Tu |
| 2004/0137059 | A1 | 7/2004 | Nivaggioli |
| 2004/0151753 | A1 | 8/2004 | Chen et al. |
| 2004/0208910 | A1 | 10/2004 | Ashton et al. |
| 2004/0234611 | A1 | 11/2004 | Ahlheim et al. |
| 2005/0107463 | A1 | 5/2005 | Woodward et al. |

(56) References Cited

U.S. PATENT DOCUMENTS

| | | |
|---|---|---|
| 2005/0112175 A1 | 5/2005 | Yaacobi |
| 2005/0113806 A1 | 5/2005 | DeCarvalho et al. |
| 2005/0175708 A1 | 8/2005 | Carrasquillo et al. |
| 2005/0192264 A1 | 9/2005 | Penfold |
| 2005/0244458 A1 | 11/2005 | Huang et al. |
| 2005/0244461 A1 | 11/2005 | Nivaggioli et al. |
| 2005/0244462 A1 | 11/2005 | Farooq |
| 2005/0244463 A1 | 11/2005 | Huang et al. |
| 2005/0244464 A1 | 11/2005 | Hughes |
| 2005/0244465 A1 | 11/2005 | Nivaggioli et al. |
| 2005/0244466 A1 | 11/2005 | Whitcup et al. |
| 2005/0244467 A1 | 11/2005 | Nivaggioli et al. |
| 2005/0244468 A1 | 11/2005 | Huang et al. |
| 2005/0244469 A1 | 11/2005 | Whitcup et al. |
| 2005/0244470 A1 | 11/2005 | Hughes et al. |
| 2005/0244471 A1 | 11/2005 | Shiah et al. |
| 2005/0244478 A1 | 11/2005 | Hughes et al. |
| 2005/0244479 A1 | 11/2005 | Huang et al. |
| 2005/0244506 A1 | 11/2005 | Burke et al. |
| 2006/0013859 A1 | 1/2006 | Yamada et al. |
| 2006/0173060 A1 | 8/2006 | Chang et al. |
| 2006/0182781 A1 | 8/2006 | Hughes |
| 2006/0246145 A1 | 11/2006 | Chang |
| 2007/0129552 A1 | 6/2007 | Donde et al. |
| 2007/0142376 A1 | 6/2007 | Fleenor et al. |
| 2007/0203222 A1 | 8/2007 | Old |
| 2007/0224246 A1 | 9/2007 | Hughes et al. |
| 2007/0233037 A1 | 10/2007 | Gifford, III et al. |
| 2007/0265330 A1 | 11/2007 | Old |
| 2008/0033351 A1 | 2/2008 | Trogden |
| 2008/0131481 A1 | 6/2008 | Hughes |
| 2008/0131482 A1 | 6/2008 | Hughes |
| 2008/0131484 A1 | 6/2008 | Robinson et al. |
| 2008/0145403 A1 | 6/2008 | Spada |
| 2008/0269498 A1 | 10/2008 | Old |
| 2008/0292679 A1 | 11/2008 | Lyons et al. |
| 2008/0312321 A1 | 12/2008 | Donde et al. |
| 2009/0082863 A1 | 3/2009 | Schieber |
| 2009/0124676 A1 | 5/2009 | Donde et al. |
| 2010/0074957 A1 | 3/2010 | Robinson et al. |
| 2010/0098772 A1 | 4/2010 | Robinson et al. |
| 2010/0104654 A1 | 4/2010 | Robinson et al. |
| 2010/0124565 A1 | 5/2010 | Spada et al. |
| 2010/0210689 A1 | 8/2010 | Old et al. |
| 2010/0247606 A1 | 9/2010 | Robinson |
| 2010/0278898 A1 | 11/2010 | Hughes et al. |
| 2010/0310637 A1 | 12/2010 | Abdulrazik |
| 2011/0160210 A1 | 6/2011 | Fleenor et al. |
| 2011/0182966 A1 | 7/2011 | Robinson |
| 2011/0250285 A1 | 10/2011 | Hughes et al. |
| 2012/0219611 A1 | 8/2012 | Hughes et al. |
| 2013/0071349 A1 | 3/2013 | Robinson et al. |

FOREIGN PATENT DOCUMENTS

| | | |
|---|---|---|
| EP | 0364417 | 9/1989 |
| EP | 0490305 | 6/1992 |
| EP | 0430539 | 10/1994 |
| EP | 1541151 | 6/2005 |
| WO | WO-94-14417 | 7/1994 |
| WO | 9513765 | 5/1995 |
| WO | WO 95/15748 | 6/1995 |
| WO | 9638174 | 12/1996 |
| WO | 99/05263 | 2/1999 |
| WO | 0004899 | 3/2000 |
| WO | WO 00/37056 | 6/2000 |
| WO | 0130323 | 5/2001 |
| WO | 0158240 | 8/2001 |
| WO | 02-02076 A2 | 1/2002 |
| WO | WO 02/05815 | 1/2002 |
| WO | WO 02/09787 | 2/2002 |
| WO | WO 02/43785 | 6/2002 |
| WO | WO 02/085248 | 10/2002 |
| WO | 03-024420 | 3/2003 |
| WO | 03020172 | 3/2003 |
| WO | WO 03/047513 | 6/2003 |
| WO | 03-074038 | 9/2003 |
| WO | 03-103772 | 12/2003 |
| WO | 2004-014352 | 2/2004 |
| WO | WO 2004/019938 | 3/2004 |
| WO | 2006-098918 A2 | 9/2004 |
| WO | 2005-110424 | 11/2005 |
| WO | WO 2005/107727 | 11/2005 |
| WO | WO-2006-063179 | 6/2006 |
| WO | 2008-070402 A2 | 6/2008 |
| WO | WO-2009-061811 | 5/2009 |
| WO | WO-2009-098458 | 8/2009 |
| WO | 2009-129187 | 10/2009 |
| WO | WO2009-132088 | 10/2009 |
| WO | 2009-143288 | 11/2009 |
| WO | 2009-143288 A1 | 11/2009 |
| WO | 2010-048086 | 4/2010 |
| WO | 2010-062523 A2 | 6/2010 |
| WO | WO-2010-093945 | 8/2010 |
| WO | 2010-111449 | 9/2010 |
| WO | 2011-014332 | 2/2011 |
| WO | 2011-075481 | 6/2011 |
| WO | 2011-091205 | 7/2011 |
| WO | WO 2011/091205 | 7/2011 |
| WO | 2011-130462 | 10/2011 |

OTHER PUBLICATIONS

Allergan, Inc., 2004, TazoracAllergan Product Information, Product Information Sheet, 0, 1-8.

Anderson et al., 1976, An Injectable Sustained Release Fertility Control System, Contraception, 13, 375-384.

Baker, 1987, Controlled Release of Biologically Active Agent, A Wiley-Interscience Publication, 0, 73-75.

Bito, 1965, Biological Protection with Prostanoids, CRC Press, Inc., 1, 231-252, Cohen, M. M., ed., Boca Raton, Fla., CRC Press Inc.

Bito, 1987, Prostaglandins, Old Concepts And New Perspectives, Archives Of Opthalmology, 105, 1036-1039.

Bito, 2001, A new approach to the medical management of glaucoma, from the bench to the clinic, and beyond. Investigative Ophthalmology & Visual Science, 42(6), 1126-1133, The Proctor Lecture.

Bito, L. Z., Jan. 1, 1984, Applied Pharmacology in the Medical Treatment of Glaucomas Drance, Glaucoma: Applied Pharmacology, 20, pp. 477-505, S. M. & Neufeld, A. H. eds., New York, Grune & Stratton.

Bodor et al., 1992, A Comparison of Intraocular Pressure Elevating Activity of Loteprednoletabonate and Dexamethasone in Rabbits, Current Eye Research, 11, 525-530.

Brubaker, 2001. Mechanism of Action of Bimaloprost (LumiganTM), Surv Ophthalmol, 45-Suppl 4, S347-S351.

Busse et al., 2001, Tyrosine Kinase Inhibitors: Rationale, Mechanisms of Action, and Implications for Drug Resistance, Semin Oncol, 28-Suppl 16, 47-55.

C.B. Camras, Dec. 1977, Reduction of Intraocular Pressure By Prostaglandins Applied topically To The Eyes Of Conscious Rabbits, Investigative Ophthalmology & Visual Science, 16(12), 1125-1134.

Cen et al., 2008, Preliminary evaluation of biodegradable implant for intraocular sustained-release of cefuroxime in rabbits, 0258, 06-0644-04, 644-647.

Charles et al., Apr. 1991, Use of Bioerodible Polymers Impregnated with Mitomycin in Glaucoma Filtration Surgery in Rabbits, Opthalmology, 98-4, 503-508.

Chen et al., Jun. 12, 2002, LumiganR: A Novel Drug for Glaucoma Therapy, Optom In Pract., 3, 95-102.

Cheng-Kuo Cheng, et al., 1995, Intravitreal Sustained-Release Dexamethasone Device In The Treatment Of Experimental Uveitas, Investigative Ophthalmology & Visual Science, 96 (2), 442-453.

Chang et al., 00/00/1996, Pharmacokinetics and Intraocular Pressure Lowering Effect of Timolol Preparations in Rabbit Eyes, Journal of Ocular Pharmacology and Therapeutics, 12-4, 471-480.

Clive, 2002, A New Ocular Hypotensive Agent for Achieving Target Intraocular Pressure, ACTA Ophthalmol Scand Scientific Abstracts, 80-4, 457.

(56) References Cited

OTHER PUBLICATIONS

Coleman et al, 00/00/2003, A 3-Month Randomized Controlled Trial of Bimatoprost (LUMIGAN) Versus Combined Timolol and Dorzolamide (Cosopt) in Patients with Glaucoma or Ocular Hypertension, Ophthalmology, 110-12, 2362-8.
Coquelet et al., Feb. 25, 2002, Successful Photodynamic Therapy Combined with Laser Photocoagulatio in Three Eyes With Classic Suboveal Choroidal Neovascularisation Affecting Two Patients With Choroiditis: Case Reports, Bull. Soc. Belge Ophthalmal, 283, 69-73.
Di Colo, 00/00/1992, Controlled Drug Release From Implantable Matrices Based on Hydrophobic Polymers, Biomaterials, 13-12, 850-856.
Enyedi et al., 1995, An Intravitreal Device Providing Sustained Release of Cyclosporins and Dexamethason, Current Eye Research, 0, 549-557.
Epstein, 00/00/1986, Primary Oepn-Angle Glaucoma, Chandler and Grant's Glaucoma, 0, 129-181.
Fabbro et al., 00/00/2002, Protein Tyrosine Kinase Inhibitors: New Treatment Modalities?, Current Opinion in Pharmacology, 2, 374-381.
Fotis et al., 00/00/1994, The Endogenous Oestrogen Metabolite 2-methoxyoestradiol inhibits Angiogeneses and Suppresses Tumour Growth, Current Opinion in Pharmacology, 237, 368.
Gil et al., Sep. 1996, Molecular characterization and ocular hypotensive effects of prostanoid EP2 receptors, Exp Eye Res, 63(Suppl 1), S104-Abstract 5.
Gilman et al., 00/00/1990, The Pharamceutical Basis of Therapeutics, Goodman and Gilman's, 8th Edition, 1447-1451.
Goel et al., 00/00/2002, Tyrosine Kinase Inhibitors: A Clinical Perspective, Current Oncology Reports, 4, 9-19.
Guenther, 00/00/2003, Optimizing Treatment with Topical Tazarotene, Am. J. Clin. Dermotol, 4-3, 197-202.
Hainsworth et al., 1996, Sustained Release Intravitreal Dexamethasone, Journal of Ocular Pharmacology and Therapeutics, 12-1, 57-63.
Haluska et al., 00/00/2001, Receptor tyrosine kinase inhibitors, Current Opinion in Investigational Drugs, 2-2, 280-286.
Hare et al., 00/00/2001, Efficacy and Safety of Memantine, an NMDA-Type Open-Channel Blocker, from Reduction of Retinal Injury associated with Experimental Glaucoma in Rat and Monkey, Sur Ophthalmol, 45-Suppl. 3, S284-S289.
Hashizoe et al., 00/00/1994, Scleral Plugof Biodegradable Polymers for Controlled Drug Release in the Vitreous, Arch Ophthalmol, 112, 1380-1384.
Heller, 1987, Biodegradable Polymers In Controlled Drug Delivery, Critical Reviews in Therapeutic Drug Carrier systems, 1 (1), 39-90.
Heller, 1987, Hydrogels in Medicine and Pharmacy, N.A. Peppes ed., III, 137-149.
Higginbotham, et al., Oct. 2002, One-Year, Randomized Study Comparing Bimatoprost And Timolol In Glaucoma And Ocular Hypertension, Archives Of Opthalmology, 120 (10), 3 Pages.
Hsu et al., 2008, Tissue bioengineering for surgical bleb defects: an animal study, Graefe's Archive for Clinical and Experimental Ophthalmology, 246(5), 709-717.
Hu et al., 2001, Effects of prostaglandin E2 and EP receptor agonists on human iridial melanocytes in vitro, Invest Ophthalmol Vis Sci, 42(4), S632, ABS 4467-B486.
Hubbard et al., 00/00/2000, Protein Tyrosine Kinase Structure and function, Annnu. Rev. Biochem., 69, 373-98.
Jackanicz et al., 00/00/1973, Polyactic Acid As A Biodegradable Carrier For Contraceptive Steroids, Contraception, 8-3, 227-235.
Jampel et al., Mar. 1990, Glaucoma Filtration Surgery in Monkeys Using 5-Fluorouridine in Polyanhydride Disks Arch Ophthalmol, 108, 430-435.
Janoria et al., Jul. 1, 2007, Novel approaches to retinal drug delivery, Expert Opinion on Drug Delivery, 4, 376-377.
Janoria, et al., 2007, Novel Approaches To Retinal Drug Delivery, Expert Opinion Drug Delivery, 4 (4), 371-388.

Kochinke et al., 00/00/1994, A New Vitreal Drug Delivery System Using an Implantable Biodegradable Polymeric Device, Invest Ophthalmol Vis Sci, 35, 2815-2819.
Kochinke et al., Feb. 15, 1996, Biodegradable Drug Delivery System for Uveitis Treatment, Investigative Ophthalmology & Visual Science, 37(3), 186-B98.
Kwak et al., 00/00/1992, Evaluation of the Retinal Toxicity and Pharmacokinetics of Dexamethasone After Intravitreal Injection, Arch. Ophthalmol, 110, 259-66.
Ladewig et al., Apr. 2005, Prostaglandin E1 infusion therapy in dry age-related macular degeneration, Prostaglandins Leukotrienes Essential Fatty Acids, 72, 251-256.
Lai et al., 00/00/2002, Alpha-2 Adrenoceptor Agonist Protects Retinal Function After Retinal Ischemic Injury in the Rat, Vis Neurosci, 19, 175-185.
Lai, 2010, Biocompatibility of chemically cross-linked gelatin hydrogels for ophthalmic use, J. Mater Sci: Mater Med, 21, 1899-1911.
Lai, 2011, Biocompatibility Assessment of Gelatin Carriers Used in Corneal Endothelial Cell Delivery, Advances in Condensed Matter and Materials, Chapter 4, 95-96.
Lee et al., Dec. 1987, Glaucoma Filtration Surgery in Rabbits Using Bioerodible Polymers and 5-Fluorouacil, Ophthalmol, 94-12, 1523-1530.
Lee et al., Nov. 1988, The Use of Bioerodible Polymers and 5-Fluorouracils in Glaucoma Filtration Surgery, Ophthalmology & Visual Science, 29-11, 1692-1697.
Marks, 00/00/2001, Topical Tazarotene:Review and Re-Evaluation, Retinoids, 17(3), 72-74.
Maruquis, et al., 2005, Management of Glaucoma: Focus On Pharmacological Therapy, Drugs & Aging, 22 (1), 1-21.
Maurice, 00/00/1983, Micropharmaceutics of the Eye, Ocular Inflammation Ther., 1, 97-102.
Mayoclinic, May 27, 2008, Stargardt's Disease: Can It Be Treated?, MayoClinic.Com, 2 Pages.
Merck Source, 2007, Analogue, Dorland's Medical Dictionary, 2 pages.
Miller et al., 00/00/1977, Degradation Rats of Oral Resorbable Implants (Polyactates and Polyglycolates): Rate Modification with Changes in PLA/PGA Copolymer Ratios, J. Biomed Materials Res, 11, 711-719.
Miller et al., 00/00/1997, Synthesis and Structure-Activity Profiles of A-Homoestranes, the Estratopones, J. Med. Chem., 40, 3836-3841.
Moss, Apr. 27, 2008, Leber's Congenital Amaurosis, TSBVI, Texas Deafblind Outrech, 3 Pages.
Muther, May 24, 2006, Development of a Resorable Anterior Chamber Glaucoma Implant, Dissertation-Rheinland-Westfalen Technical College, 1-96.
Nam et al., 1999, Protein loaded biodegradable microspheres based on PLGA/protein bioconjugates, J. Microencapsulation, 16(5), 625-637.
Newman, 2005, Hereditary Optic Neuropaths: From The Mitochandria To The Optic Nerve, American Journal Of Ophthalmology, 140(3), 517e1-517e8.
Nilsson, 1987, PGF 2a Increases Uveoscleral Outflow, Invest. Ophthalmol. Vis. Sci. 28 (Suppl), 284.
Nordstrom et al., 2005, Persistence and Adherence With Topical Glaucoma Therapy, American Journal of Ophthalmology, 140, 598-608.
Nordstrom et al., May 2005, Use of Surodex in Phacotrabeculectomy Surgery, Am J Ophthalmol, 139(5), 927-928.
Occulex, Aug. 6, 2002, Oculex Announces Positive Clinical Results for Posurdex(r) the first biodegradable ocular implant, PR Newswire, 1-2.
Olsen et al., 1995, Human Scleral Permeability: Effects of Age, Cryotherapy, Transcleral Diode Laser, and Surgical Thinning, Invest, Ophthalmol. Vis. Sci., 36, 1893-1903.
Philip E.J. Hoyng, 2000, Pharmacological Therapy For Glaucoma, Drugs 2000, 59 (3), 411-434.
Phillips et al., 11/00/2002, Efficacy of 0.1% Tazarotene Cream for the treatment of Photodamage, Arch Dermatol, 138(11), 1486-1493.

(56) References Cited

OTHER PUBLICATIONS

Phillips et al., 1985, Penetration of Timolol Eye Drops into Human Aqueous Humor: The First Hour, British Journal of Ophthalmology, 69, 217-218.
Pribluda et al., 00/00/2000, 2-Methoxyestradiol: An Endogenous Antiangionic and Antiproliferative Drug Candidate, Cancer and Metastasis Reviews, 19, 173-179.
Quigley et al, 00//00/1980, The Mechanism of Optic Nerve Damage in Experimental Acute Intraocular Pressure Elevation, Invest. Ophthalmol. Vis. Sci., 19, 505-517.
Rao et al., 1997-1998, Intraocular Inflammation and Uveitis, Basic and Clinical Science Course(San Francisco: American Academy of Ophthalmology, 9, 57-80, 102-103, 152-156.
Renfro et al., 00/00/1992, Ocular Effects of Topical and Systemic Steroids, Dermatologic Clinics, 10, 505-512.
Schonfeld, Mar. 1, 2001, Lumigan Found Effective Early Phase 3, Ocul. Surg. News, 19(5)1,35.
Schuettauf et al., 00/00/2002, Effects of anti-glaucoma Medications on Ganglion Cell Survival: the DBA/2J Mouse Model, Vision Res., 42(20), 2333-2337.
Schumacher et al., 00/00/2001, The Physiological Estrogen Metabolite 2-Methoxyestradiol Reduced Tumor Growth and Induces Apoptosis in Human Solid Tumors, J Cancer Res Clin Oncol, 127, 405-410.
Schwartz, 00/00/1966, The Response of Ocular Pressure to Corticosteroids, Ophthamol. Clin. North Am., 6, 929-989.
Siebold et al., Feb. 1, 1989, Esterified Prostaglandin Shows 'Potent' Promise, Ocular Surgery News, 1, pp. 3, 59.
Skalka et al., 00/00/1980, Effect of Corticosteroids on Cataract Formation, Arch. Ophthalmol, 98, 1773-1777.
Smith et al., Sep. 1996, Sustained-Release Subconjunctival 5-Fluorouracil, Ophthalmic Surgery and Laser, 27-9, 763-767.
Spaeth, et al., 1977, Steroid-induced Glaucoma: A Persistent Elevatioin Of Intraocular Pressure B, Hisopathological Aspects, Th. Am. Ophth. Soc. vol. LXXV, 353-381.
Starr, 1971, further Studies on the Effects of Prostagladin on Intraocular Pressure in the Rabbit, Exp. Eye Res., 11, 170-177.
Tan et al., Dec. 2001, Randomized Clinical Trial of Serodex Steroid Drug Delivery system for Cataract Surgery: Anteriror Versus Posterior Placement of Two Surodex in the Eye, Ophthalmology, 108(12), 2172-2181.
Tan, Feb. 1999, Randomized Clinical Trial Of a New Dexamethasone Delivery System (Surodex) For Treatment Of Post-Cataract Surgery Inflammation, Ophthalmology, 106 (2), 223-231.
Tazarotene, Drugs Future, 208-209-2003.
Tracy et al., 00/00/1998, Factors Affecting the Degradation Rate of Poly(actide-co-glycolide) Microspheres in Vivo and in Vitro, Biomaterials, 20, 1057-1062.
U.S. Appl. No. 10/966,764, filed May 12, 2005.
U.S. Appl. No. 10/246,864, filed Sep. 18, 2002.
U.S. Appl. No. 10/259,703, filed Sep. 27, 2002.
U.S. Appl. No. 10/327,018, filed Dec. 20, 2002.
U.S. Appl. No. 10/340,237, filed Jan. 9, 2003.
U.S. Appl. No. 10/836,880, filed Apr. 30, 2004.
U.S. Appl. No. 10/836,904, filed Apr. 30, 2004.
U.S. Appl. No. 10/836,908, filed Apr. 30, 2004.
U.S. Appl. No. 10/837,142, filed Apr. 30, 2004.
U.S. Appl. No. 10/837,143, filed Apr. 30, 2004.
U.S. Appl. No. 10/837,291, filed Apr. 30, 2004.
International Search Report for U.S. Appl. No. 12/411,250.
U.S. Appl. No. 10/837,348, filed Apr. 30, 2004.
U.S. Appl. No. 10/837,356, filed Apr. 30, 2004.
U.S. Appl. No. 10/837,361, filed Apr. 20, 2004.
U.S. Appl. No. 10/837,379, filed Apr. 30, 2004.
U.S. Appl. No. 11/039,192, filed Aug. 18, 2005.
U.S. Appl. No. 11/303,462, filed Dec. 15, 2005.
U.S. Appl. No. 11/368,845, filed Mar. 6, 2006.
U.S. Appl. No. 11/371,118, filed Mar. 8, 2006.
U.S. Appl. No. 11/395,019, filed Mar. 31, 2006.
U.S. Appl. No. 11/455,392, filed Dec. 20, 2007.
U.S. Appl. No. 11/552,835, filed Apr. 24, 2008.
U.S. Appl. No. 11/741,366, filed Sep. 27, 2007.
U.S. Appl. No. 11/859,627, filed Mar. 26, 2009.
U.S. Appl. No. 11/952,927, filed Dec. 7, 2007.
U.S. Appl. No. 11/952,938, filed Dec. 7, 2007.
U.S. Appl. No. 12/028,762, filed Feb. 8, 2008.
U.S. Appl. No. 12/028,763, filed Feb. 8, 2008.
U.S. Appl. No. 12/259,153, filed Oct. 27, 2008.
U.S. Appl. No. 12/355,709, filed Jan. 16, 2009.
U.S. Appl. No. 12/411,250, filed Mar. 25, 2009.
U.S. Appl. No. 13/152,780, filed Jun. 3, 2011.
U.S. Appl. No. 60/567,339, filed Apr. 30, 2004.
U.S. Appl. No. 60/567,423, filed Apr. 30, 2004.
U.S. Appl. No. 11/552,630, filed Feb. 7, 2008.
U.S. Appl. No. 10/836,911, filed Apr. 30, 2004.
Wadood, Apr. 2004, Safety And Efficacy Of A Dexamethasone Anterior Segment Delivery System In Patients After Phacoemulsification, Journal of Cataract And Refractive Surgery, 30, 761-768.
Watson et al., 00/00/1996, A Six-month, Randomized, Double-masked Study Comparing Latanoprost with Timolol in Open-Angle Glaucoma and Ocular Hypertension, Ophthalmology, 103, 126-137.
Wheeler et al., 04/00/2003, Role of Alpha-2-Agonist in Neuroprotection, Sur Ophthalmol, 48(Suppl 1), S47-S51.
Wheeler, 00/00/1999, Experimental Study of Agents with Potential Neuroprotective Properties, Acta Ophthalmol Scand, 77, 27-28.
Woldemussie, 00/00/2002, Neuroprotection Effects of Memantine in Different Retinal Injury Models Glaucoma, J Glaucoma, 11(6), 474-480.
Woldemussie, 2000, Neuroprotection of Retinal Ganglion Cells in Experimental Models of Glaucoma, Minerva Ophthalmol, 42(2), 71-78.
Woodward et al., 00/00/2001, The Pharmacology of Bimatoprost (LumiganTM), Surv Ophthalmol, (Suppl 4), S337-S345.
Woodward et al., Feb. 1997, The molecular biology and ocular distribution of prostanoid receptors, Surv Ophthalmol, 41(Suppl 2), S15-S21.
Woodward et al., Sep. 1996, Eicosanoid Receptors: Pharmacology and Ocular Distribution, Exp Eye Res. 63(Suppl 1), S23-Abstract 2.
Woodward, 00/00/2002, AGN 192024 (LumiganR): A Synthetic Prostamide Analog that Lowers Primate Intraocular Pressure by Virtue of Its Inherent Pharmacological Activity, ARVO Abstract, 1 page.
Woodward, 2007, Fixed-Combination and Emerging Glaucoma Therapies, 12(2), 313-327, Expert Opin. Emerging Drugs.
Zhou, et al., 1998, Develop Of A Multiple-Drug Delivery Implant For Intraocular Management Of Proliferative Vitreoretinopathy, Journal of Controlled Release, 55, 281-295, Elsevier.
Heller; Biodegradable Polymers in Controlled Drug Delivery, CRC Critical Reviews in Therapeutic Drug Carrier Systems, vol. 1, CRC Press, Boca Raton, FL, pp. 39-90.
International Search Report in PCT/US2011/032393.
U.S. Appl. No. 61/287,078, filed Dec. 16, 2009.
U.S. Appl. No. 61/297,660, filed Jan. 22, 2010.
U.S. Appl. No. 10/837,260, filed Apr. 30, 2004.
U.S. Appl. No. 11/565,917, filed Dec. 1, 2006.
U.S. Appl. No. 12/255,497, filed Oct. 21, 2008.
U.S. Appl. No. 13/011,467, filed Jan. 21, 2011.
U.S. Appl. No. 13/466,752, filed May 8, 2012.
U.S. Appl. No. 13/466,804, filed May 8, 2012.
U.S. Appl. No. 13/511,548, filed May 23, 2012.
Heys et al, "A Boussinesq model of natural convection in the human eye and the formation of Krukenberg's spindle", Annals of Biomedical Engineering, vol. 30, pp. 392-401, Jan. 1, 2002.
International Search Report and the Written Opinion of the International Searching Authority for International application No. PCT/US2010/028584, mailed Aug. 3, 2010.
International Search Report and the Written Opinion of the International Searching Authority for International application No. PCT/US2011/021971, mailed Jan. 26, 2012.
Moshfeghi et al, "Retinal and Choroidal Vascular Occlusion After Posterior Sub-Tenon Triamcinolone Injection", American Journal of Ophthalmology, vol. 134, Issue 1, 2002, pp. 132-134.
Stewart et al, "The Efficacy and Safety of Latanoprost 0.005% Once Daily Versus Brimonidine 0.2% Twice Daily in Open-Angle Glau-

(56) References Cited

OTHER PUBLICATIONS coma or Ocular Hypertension", American Journal of Ophthalmology, vol. 131, Issue 5, 2001, pp. 631-635.

United States Board of Patent Appeals and Interferences decision on appeal in *Ex parte* Nivaggioli et al., Appeal No. 2009-013914, U.S. Appl. No. 10/340,237, mailed Sep. 21, 2010.

United States Board of Patent Appeals and Interferences decision on appeal in *Ex parte* Huang et al., Appeal No. 2010-006865, U.S. Appl. No. 10/836,880, mailed Sep. 28, 2010.

United States Board of Patent Appeals and Interferences decision on appeal in *Ex parte* Huang et al., Appeal No. 2010-004999, U.S. Appl. No. 10/836,911, mailed Oct. 25, 2010.

United States Board of Patent Appeals and Interferences decision on appeal in *Ex parte* Hughes et al., Appeal No. 2011-003859, U.S. Appl. No. 11/116,698, mailed Aug. 1, 2011.

Kivalo et al, "Biodegradable tube implants in experimental glaucoma surgery in the rabbit", Journal of Materials Science: Materials in Medicine 10 (1999) 53-58.

Shi et al, "FK506 in a Biodegradable Glycolide-co-Clatide-co-Caprolactone Polymer for Prolongation of Corneal Allograft Survival", Current Eye Research, 30, 969-976, 2005.

Short, Brian G., "Safety Evaluation of Ocular Drug Delivery Formulations: Techniques and Practical Considerations", Toxicologic Pathology, 36, 49-62, 2008.

Theng et al, "Pharmacokinetic and Toxicity Study of an Intraocular Cyclosporine DDS in the Anterior Segment of Rabbit Eyes", IOVS, Nov. 2003, vol. 44, No. 11.

USP 23; NF 18 (1995) pp. 1790-1798.

\* cited by examiner

A slit lamp photograph through a gonioscopy lens showing an intracameral bimatoprost implant adjacent to the trabecular meshwork in the dog eye.

Dilated vessels (arrows) represent outflow vessels in a dog that received a high-release bimatoprost intracameral implant described in greater detail in Example 1

Dilated vessels (arrows) represent outflow vessels in a dog that received a low-release bimatoprost intracameral implant described in greater detail in Example 2

INTRAOCULAR PRESSURE REDUCTION WITH INTRACAMERAL BIMATOPROST IMPLANTS

CROSS REFERENCE TO RELATED APPLICATIONS

This application is a continuation in part of U.S. patent application Ser. No. 10/837,260, filed on Apr. 30, 2004 in the names of Hughes et al, incorporated entirely by reference.

BACKGROUND OF THE INVENTION

1. Field of the Invention

The present invention relates to a method of treating an ocular condition, comprising the step of placing a biodegradable intraocular implant in an eye of the patient, the implant comprising a prostamide and a biodegradable polymer matrix that releases drug at a rate effective to sustain release of an amount of the prostamide from the implant to provide an amount of the prostamide effective to prevent or reduce a symptom of the ocular condition, wherein said ocular condition is elevated IOP.

2. Summary of the Related Art

The anterior and posterior chambers of the eye are filled with aqueous humor, a fluid predominantly secreted by the ciliary body with an ionic composition similar to the blood. The function of the aqueous humor is two-fold: to 1) supply nutrients to the avascular structures of the eye, such as the lens and cornea and 2) maintain intraocular pressure (IOP) within its physiological range. Maintenance of IOP and supply of nutrients to the anterior segment are factors that are critical for maintaining normal visual acuity. Aqueous humor is predominantly secreted to the posterior chamber of the eye by the ciliary processes of the ciliary body and a minor mechanism of aqueous humor production is through ultrafiltration from arterial blood. Aqueous humor then reaches the anterior chamber by crossing the pupil and there are convection currents where the aqueous, adjacent to the iris, flows upwards, and the aqueous, adjacent to the cornea, flows downwards. There are two different pathways of aqueous humor outflow, both located in the iridocorneal angle of the eye. The uveoscleral or nonconventional pathway refers to the aqueous humor leaving the anterior chamber by diffusion through intercellular spaces among ciliary muscle fibers. Although this seems to be a minority outflow pathway in humans, the uveoscleral or nonconventional pathway is the target of specific anti-hypertensive drugs such as the hypotensive lipids, e.g. bimatoprost, that increase the functionality of this route through remodeling of the extracellular matrix. In addition, bimatoprost may improve aqueous outflow through the trabecular meshwork ("TM") mediated through a prostamide receptor. In the human eye, the main outflow route is the trabecular or conventional outflow pathway. This tissue contains three differentiated layers. From the inner to the outermost part, the layer of tissue closest to the anterior chamber is the uveal meshwork, formed by prolongations of connective tissue arising from the iris and ciliary body stromas and covered by endothelial cells. This layer does not offer much resistance to aqueous humor outflow because intercellular spaces are large. The next layer, known as the corneoscleral meshwork, is characterized by the presence of lamellae covered by endothelium-like cells on a basal membrane. The lamellae are formed by glycoproteins, collagen, hyaluronic acid, and elastic fibers. The higher organization of the corneoscleral meshwork in relation to the uveal meshwork as well as their narrower intercellular spaces are responsible for the increase in flow resistance. The third layer, which is in direct contact with the inner wall of endothelial cells from Schlemm's canal, is the juxtacanalicular meshwork. It is formed by cells embedded in a dense extracellular matrix, and the majority of the tissue resistance to aqueous flow is postulated to be in this layer, due to its narrow intercellular spaces. The layer of endothelial cells from Schlemm's canal has expandable pores that transfer the aqueous into the canal and accounts for approximately 10% of the total resistance. It has been postulated that aqueous humor crosses the inner wall endothelium of Schlemm's canal by two different mechanisms: a paracellular route through the junctions formed between the endothelial cells and a transcellular pathway through intracellular expandable pores of the same cells. Once there is entry into Schlemm's canal, the aqueous drains directly into the collector ducts and aqueous veins that anastomose with the episcleral and conjunctival plexi of vessels. Aqueous humor outflow via the trabecular pathway is IOP dependent, usually measured as outflow facility, and expressed in microliters per minute per millimeter of mercury. The episcleral venous pressure controls outflow through the collector channels and is one factor that contributes to the intraocular pressure. Increases in the episcleral venous pressure such as seen with carotid-cavernous sinus fistulas, orbital varices, and Sturge-Weber Syndrome, can lead to difficult to manage glaucoma. Reducing episcleral venous pressure in disease states, such as treating carotid-cavernous sinus fistulas, can normalize the episcleral venous pressure and reduce the intraocular pressure. The mechanism of action of modern ocular hypotensive agents for treating ocular hypertension and open angle glaucoma are as follows: 1—reduce aqueous humor production, 2—improve uveoscleral outflow, 3—improve outflow through the TM with miotic agents by providing tension as the scleral spur with stimulation of the ciliary body muscle, 4—combination of any of the above.

BRIEF SUMMARY OF THE INVENTION

Unexpectedly, when sustained-release implants releasing bimatoprost were placed in an intracameral location, the outflow channels emanating from Schlemm's Canal were visibly dilated (See FIG. 4). This results in a profound reduction in the intraocular pressure, i.e. −60% IOP reduction from baseline. (See FIG. 5), This reduction is significantly more than what is typically observed with topical bimatoprost, i.e. −35% IOP reduction) The redirection of aqueous flow towards the TM is illustrated in FIG. 1, lower image. The usual mechanism of prostamides is to remodel both the anterior ciliary body near the ciliary band and the TM. The intracameral implants, which are located adjacent to the TM, as shown in FIG. 3, provide a high drug concentration into the outflow channels and dilate the vessels in the episcleral and conjunctival venous plexus, thereby resulting in a novel mechanism of IOP reduction. The dilation appears 360 degrees around the eye since drug released from an implant positioned at the 6:00 O'clock position is well-mixed throughout the anterior segment through the convection currents.

This incremental reduction in the IOP with the intracameral bimatoprost implants is advantageous for patients with ocular hypertension and open angle glaucoma that require sustained reduction in IOP to prevent progressive optic neuropathy. Patients can avoid the need for combination eye drops and/or surgery (including incisional surgery such as trabeculectomy, laser procedures such as ALT and SLT, and aqueous humor bypass stents), if they are able to achieve profound reductions in IOP with the intracameral implant described herein.

BRIEF DESCRIPTION OF THE DRAWINGS

FIG. 1 (lower image) shows an intracameral sustained-release bimatoprost implant releasing drug directly into Schlemm's canal resulting in visible dilation of the outflow channels.

DETAILED DESCRIPTION OF THE INVENTION

Figure 1:
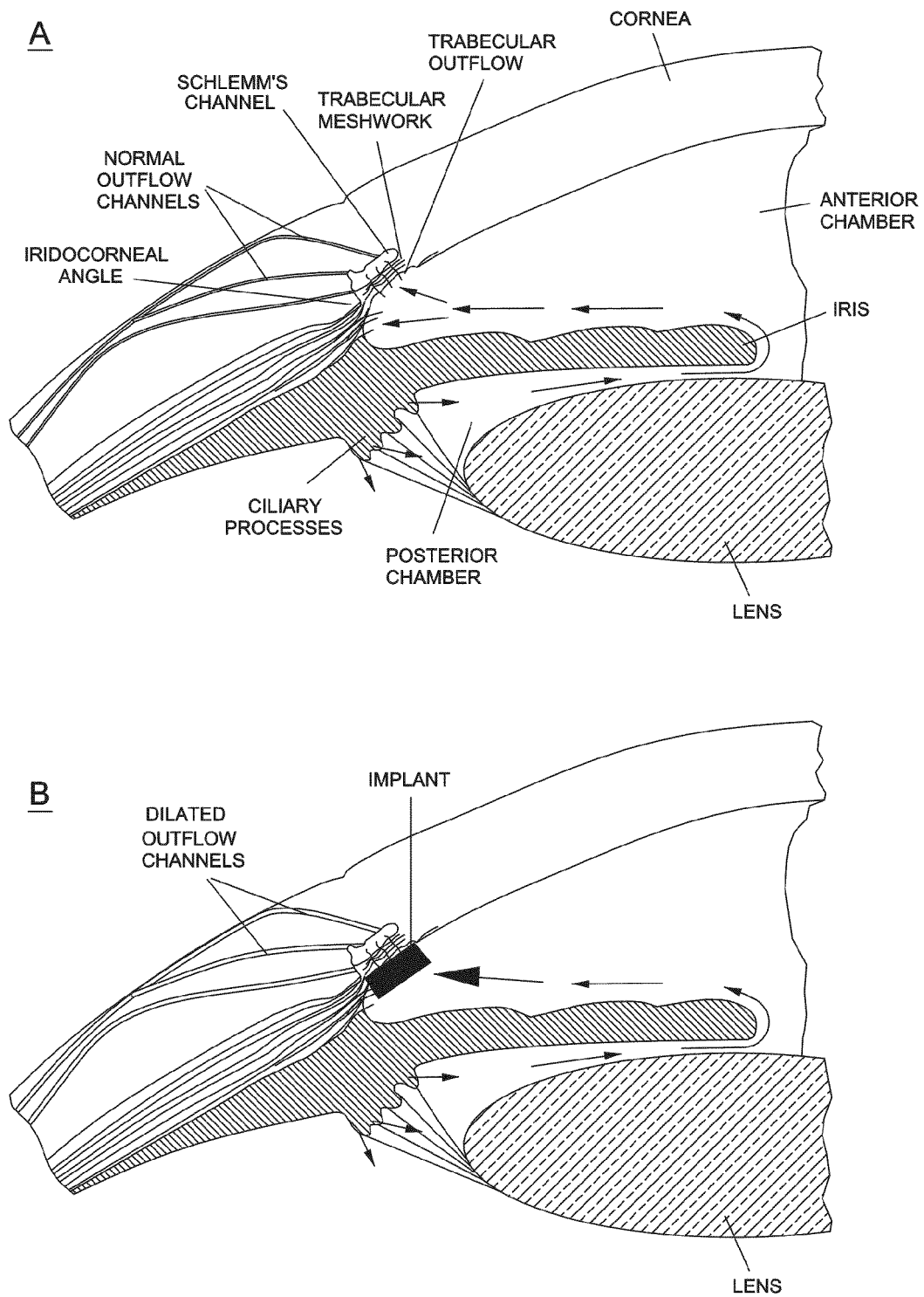
FIG. 1 (upper image) shows aqueous humor is predominantly secreted to the posterior chamber of the eye by the ciliary processes of the ciliary body.
Figure 2:
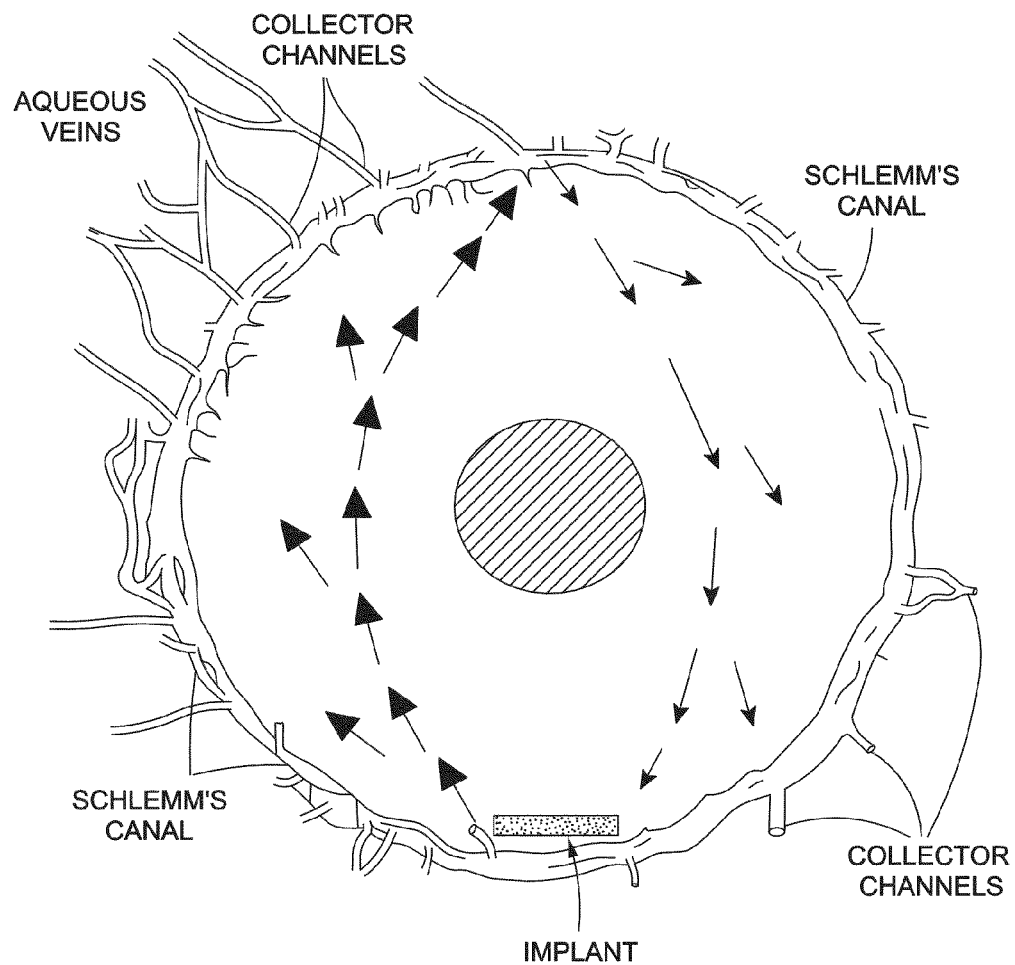
FIG. 2 shows that aqueous humor reaches the anterior chamber by crossing the pupil and there are convection currents where the flow of aqueous adjacent to the iris is upwards, and the flow of aqueous adjacent to the cornea is downwards.
Figure 3:
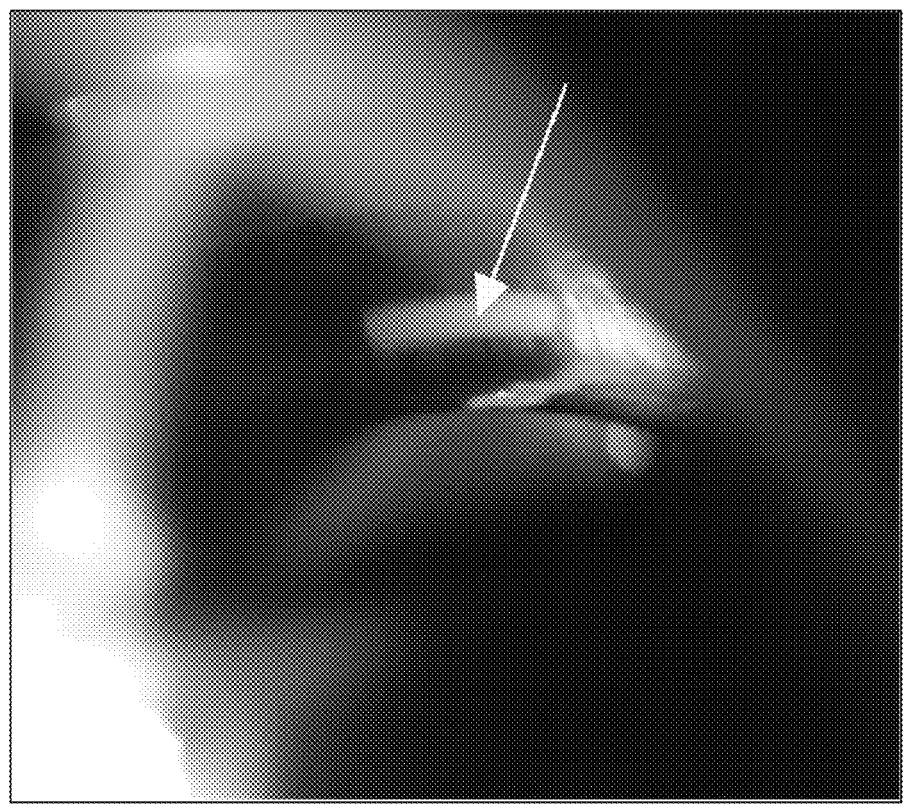
FIG. 3 is a slit lamp photograph through a gonioscopy lens showing an intracameral bimatoprost implant placed adjacent to the trabecular meshwork in the dog eye.

As disclosed herein, controlled and sustained administration of a therapeutic agent through the use of one or more intraocular implants may improve treatment of undesirable ocular conditions, in particular elevated IOP. The implants comprise a pharmaceutically acceptable polymeric composition and are formulated to release one or more pharmaceutically active agents, such as a prostamide, over an extended period of time. The implants are effective to provide a therapeutically effective dosage of the agent or agents directly to a region of the eye to treat or prevent one or more undesirable ocular conditions. Thus, with a single administration, therapeutic agents will be made available at the site where they are needed and will be maintained for an extended period of time, rather than subjecting the patient to repeated injections or repeated administration of topical drops.

The above implants are utilized in a method of treating an ocular condition, comprising the step of placing a biodegradable intraocular implant in an eye of the patient, the implant comprising a prostamide and a biodegradable polymer matrix that releases prostamide at a rate effective to sustain an amount of prostamide effective to prevent or reduce a symptom of the ocular condition, wherein said ocular condition is elevated IOP and said implant is placed in an intracameral location to dilate the outflow channels of the eye emanating from Schlemm's Canal.

An intraocular implant in accordance with the disclosure herein comprises a therapeutic component. The therapeutic component comprises, consists essentially of, or consists of, a prostamide. A drug release sustaining component may be associated with the therapeutic component to sustain release of an effective amount of the prostamide into an eye in which the implant is placed. The amount of the prostamide is released into the eye for a period of time greater than about one week after the implant is placed in the eye, and is effective in treating or reducing a symptom of an ocular condition.

The implant is made of polymeric materials to provide maximal approximation of the implant to the iridocorneal angle. In addition, the size of the implant, which ranges from a diameter of approximately 0.1 to 1 mm, and lengths from 0.1 to 6 mm, enables the implant to be inserted into the anterior chamber using an applicator with a small gauge needle ranging from 22 to 30G.

Definitions

For the purposes of this description, we use the following terms as defined in this section, unless the context of the word indicates a different meaning.

As used herein, an "intraocular implant" refers to a device or element that is structured, sized, or otherwise configured to be placed in an eye. Intraocular implants are generally biocompatible with physiological conditions of an eye and do not cause adverse side effects. Intraocular implants may be placed in an eye without disrupting vision of the eye.

As used herein, a "therapeutic component" refers to a portion of an intraocular implant comprising one or more therapeutic agents or substances used to treat a medical condition of the eye. The therapeutic component may be a discrete region of an intraocular implant, or it may be homogenously distributed throughout the implant. The therapeutic agents of the therapeutic component are typically ophthalmically acceptable, and are provided in a form that does not cause adverse reactions when the implant is placed in an eye.

As used herein, a "drug release sustaining component" refers to a portion of the intraocular implant that is effective to provide a sustained release of the therapeutic agents of the implant. A drug release sustaining component may be a biodegradable polymer matrix, or it may be a coating covering a core region of the implant that comprises a therapeutic component.

As used herein, "associated with" means mixed with, dispersed within, coupled to, covering, or surrounding.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically induced avascular regions, the macula, and the retina.

As used herein, an "ocular condition" is a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

The term "biodegradable polymer" refers to a polymer or polymers which degrade in vivo, and wherein erosion of the polymer or polymers over time occurs concurrent with or subsequent to release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

The term "treat", "treating", or "treatment" as used herein, refers to reduction or resolution or prevention of an ocular condition, ocular injury or damage, or to promote healing of injured or damaged ocular tissue. A treatment is usually effective to reduce at least one symptom of an ocular condition, ocular injury or damage.

The term "effective" as used herein, refers to the level or amount of agent needed to treat an ocular condition, or reduce or prevent ocular injury or damage without causing significant negative or adverse side effects to the eye or a region of the eye. In view of the above, a therapeutically effective amount of a therapeutic agent, such as a prostamide, is an amount that is effective in reducing at least one symptom of an ocular condition.

Intraocular implants have been developed which can release drug loads over various time periods. These implants, which when inserted into an eye, such as the vitreous of an eye, provide therapeutic levels of a prostamide for extended periods of time (e.g., for about 1 week or more). The disclosed implants are effective in treating ocular conditions, such as ocular conditions associated with elevated intraocular pressure, and more specifically in reducing at least one symptom of glaucoma.

In one embodiment of the present invention, an intraocular implant comprises a biodegradable polymer matrix. The biodegradable polymer matrix is one type of a drug release-sustaining component. The biodegradable polymer matrix is effective in forming a biodegradable intraocular implant. The biodegradable intraocular implant comprises a prostamide associated with the biodegradable polymer matrix. The matrix degrades at a rate effective to sustain release of an amount of the prostamide for a time greater than about one week from the time in which the implant is placed in ocular region or ocular site, such as the vitreous of an eye.

The prostamide component of the implant includes one or more types of prostamides. In certain implants, the prostamide component comprises a compound having the formula (I).

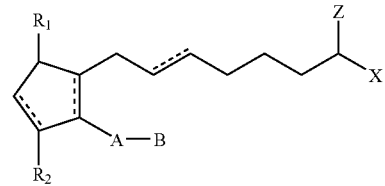

wherein the dashed bonds represent a single or double bond which can be in the cis or trans configuration, A is an alkylene or alkenylene radical having from two to six carbon atoms, which radical may be interrupted by one or more oxide radicals and substituted with one or more hydroxy, oxo, alkyloxy or alkylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is —N($R^4$)$_2$ wherein $R^4$ is independently selected from the group consisting of hydrogen and lower alkyl radicals having from one to six carbon atoms, Z is =O; one of $R_1$ and $R_2$ is =O, —OH or a —O(CO)$R_6$ group, and the other one is —OH or —O(CO)$R_6$, or $R_1$ is =O and $R_2$ is H; wherein $R_6$ is a saturated or unsaturated acyclic hydrocarbon group having from 1 to about 20 carbon atoms, or —(CH$_2$)mR$_7$ wherein m is 0-10, and $R_7$ is cycloalkyl radical, having from three to seven carbon atoms, or a hydrocarbyl aryl or heteroaryl, as defined above; or a pharmaceutically-acceptable salt thereof or a pharmaceutically-acceptable salt thereof.

Pharmaceutically acceptable acid addition salts of the compounds of the invention are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

Preferably, the prostamide has the following formula (II)

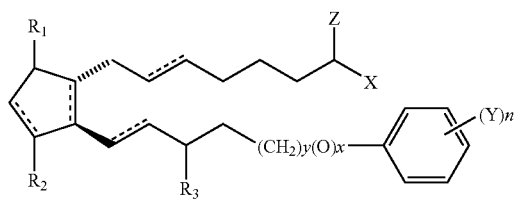

wherein y is 0 or 1, x is 0 or 1 and x+y are not both 1, Y is a radical selected from the group consisting of alkyl, halo, nitro, amino, thiol, hydroxy, alkyloxy, alkylcarboxy and halo substituted alkyl, wherein said alkyl radical comprises from one to six carbon atoms, n is 0 or an integer of from 1 to 3 and $R_3$ is .=O, —OH or —O(CO)$R_6$ and hatched lines indicate the .alpha. configuration and solid triangles indicate the .beta. configuration.

In at least one type of intraocular implant, the prostamide comprises a compound wherein $R_1$, $R_2$ and $R_3$ are OH, y is 1, x is 0, n is 0 and X is N(H)(C$_2$H$_5$), e.g. cyclopentane N-ethyl heptenamide-5-cis-2-(3α-hydroxy-5-phenyl-1-trans-pentenyl)-3,5-dihydroxy, [1$_\alpha$,2$_\beta$,3$_\alpha$,5$_\alpha$].

The compound, cyclopentane N-ethyl heptenamide-5-cis-2-(3α.-hydroxy-5-phenyl-1-trans-pentenyl)-3,5-dihydroxy, [1$_\alpha$,2$_\beta$,3$_\alpha$,5$_\alpha$], is also known as bimatoprost and is publicly available in a topical ophthalmic solution under the tradename, Lumigan.RTM. (Allergan, Inc., CA).

Alternatively, the prostamide may be any of the prostamides disclosed in U.S. Pat. No. 6,395,787, which is hereby incorporated by reference.

Thus, the implant may comprise a therapeutic component which comprises, consists essentially of, or consists of bimatoprost, a salt thereof, or mixtures thereof.

The prostamide may be in a particulate or powder form and it may be entrapped by the biodegradable polymer matrix. Usually, prostamide particles will have an effective average size less than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers.

The prostamide of the implant is preferably from about 10% to 90% by weight of the implant. More preferably, the prostamide is from about 20% to about 80% by weight of the implant. In a preferred embodiment, the prostamide comprises about 20% by weight of the implant (e.g., 15%-25%). In another embodiment, the prostamide comprises about 50% by weight of the implant.

Suitable polymeric materials or compositions for use in the implant include those materials which are compatible, that is biocompatible, with the eye so as to cause no substantial interference with the functioning or physiology of the eye. Such materials preferably are at least partially and more preferably substantially completely biodegradable or bioerodible.

Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present implants.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyvinyl alcohol, polyesters, polyethers and combinations thereof which are biocompatible and may be biodegradable and/or bioerodible.

Some preferred characteristics of the polymers or polymeric materials for use in the present invention may include biocompatibility, compatibility with the therapeutic component, ease of use of the polymer in making the drug delivery systems of the present invention, a half-life in the physiological environment of at least about 6 hours, preferably greater than about one day, not significantly increasing the viscosity of the vitreous, and water insolubility.

The biodegradable polymeric materials which are included to form the matrix are desirably subject to enzymatic or hydrolytic instability. Water-soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer and hence the extended release profile of the implant is the relative average molecular weight of the polymeric composition employed in the implant. Different molecular weights of the same or different polymeric compositions may be included in the implant to modulate the release profile. In certain implants, the relative average molecular weight of the polymer will range from about 9 to about 64 kD, usually from about 10 to about 54 kD, and more usually from about 12 to about 45 kD.

In some implants, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the implant, where a more flexible implant is desirable for larger geometries. The % of polylactic acid in the polylactic acid polyglycolic acid (PLGA) copolymer can be 0-100%, preferably about 15-85%, more preferably about 35-65%. In some implants, a 50/50 PLGA copolymer is used.

The biodegradable polymer matrix of the intraocular implant may comprise a mixture of two or more biodegradable polymers. For example, the implant may comprise a mixture of a first biodegradable polymer and a different second biodegradable polymer. One or more of the biodegradable polymers may have terminal acid groups.

Release of a drug from an erodible polymer is the consequence of several mechanisms or combinations of mechanisms. Some of these mechanisms include desorption from the implant's surface, dissolution, diffusion through porous channels of the hydrated polymer and erosion. Erosion can be bulk or surface or a combination of both. As discussed herein, the matrix of the intraocular implant may release drug at a rate effective to sustain release of an amount of the prostamide component for more than one week after implantation into an eye. In certain implants, therapeutic amounts of the prostamide component are released for no more than about 30-35 days after implantation. For example, an implant may comprise bimatoprost, and the matrix of the implant degrades at a rate effective to sustain release of a therapeutically effective amount of bimatoprost for about one month after being placed in an eye. As another example, the implant may comprise bimatoprost, and the matrix releases drug at a rate effective to sustain release of a therapeutically effective amount of bimatoprost for more than forty days, such as for about six months.

One example of the biodegradable intraocular implant comprises a prostamide associated with a biodegradable polymer matrix, which comprises a mixture of different biodegradable polymers. At least one of the biodegradable polymers is a polylactide having a molecular weight of about 63.3 kD. A second biodegradable polymer is a polylactide having a molecular weight of about 14 kD. Such a mixture is effective in sustaining release of a therapeutically effective amount of the prostamide for a time period greater than about one month from the time the implant is placed in an eye.

Another example of a biodegradable intraocular implant comprises an prostamide associated with a biodegradable polymer matrix, which comprises a mixture of different biodegradable polymers, each biodegradable polymer having an inherent viscosity from about 0.16 dl/g to about 1.0 dl/g. For example, one of the biodegradable polymers may have an inherent viscosity of about 0.3 dl/g. A second biodegradable polymer may have an inherent viscosity of about 1.0 dl/g. Additional implants may comprise biodegradable polymers that have an inherent viscosity between about 0.2 dl/g and 0.5 dl/g. The inherent viscosities identified above may be determined in 0.1% chloroform at 25.degree. C.

One particular implant comprises bimatoprost associated with a combination of two different polylactide polymers. The bimatoprost is present in about 20% by weight of the implant. One polylactide polymer has a molecular weight of about 14 kD and an inherent viscosity of about 0.3 dl/g, and the other polylactide polymer has a molecular weight of about 63.3 kD and an inherent viscosity of about 1.0 dl/g. The two polylactide polymers are present in the implant in a 1:1 ratio. Such an implant may be effective in releasing the bimatoprost for more than two months. The implant is provided in the form of a rod or a filament produced by an extrusion process.

A preferred implant formulation for the invention is API 30%, R203S 45%, R202H 20%, PEG 3350 5% or API 20%, R203S 45%, R202H 10%, RG752S 20%, PEG 3350 5%, wherein the API is bimatoprost. The range of concentrations of the constituents that can be used in the preferred implant formulation are API 5 to 40%, R203S 10 to 60%, R202H 5 to 20%, RG752S 5 to 40%, PEG 3350 0 to 15%. The PLA/PLGA polymers are from the Resomer product line available from Boehringer Ingelheim in Ingelheim, Germany and include the following:

| Resomer | Monomer ratio | i.v. dL/g |
| --- | --- | --- |
| RG502, | 50:50 poly (D,L-lactide-co-glycolide) | 0.2 |
| RG502H, | 50:50 poly (D,L-lactide-co-glycolide) | 0.2 |
| RG503, | 50:50 poly (D,L-lactide-co-glycolide) | 0.4 |
| RG504, |  | 0.5 |
| RG505, |  | 0.7 |
| RG506, |  | 0.8 |
| RG752, | 75:25 poly (D,L lactide-co-glycolide) | 0.2 |
| RG755, | 75:25 poly(D,L lactide-co-glycolide) | 0.6 (40000) |
| RG756, |  | 0.8 |
| RG858, | 85:15 poly (D,L-lactide-co-glycolide) | 1.4 |
| R202H, | poly (D,L-lactide) | 0.3 |
| R203 | poly (D,L-lactide) | 1.0 (40000) |
| R206. | poly (D,L-lactide); acid end | 0.2 |
| R104 | poly (D,L-lactide) | (3500) |

The release of the prostamide from the intraocular implant comprising a biodegradable polymer matrix may include an initial burst of release followed by a gradual increase in the amount of the prostamide released, or the release may include an initial delay in release of the prostamide component followed by an increase in release. When the implant is substantially completely degraded, the percent of the prostamide that has been released is about one hundred. Compared to existing implants, the implants disclosed herein do not completely release, or release about 100% of the prostamide, until after about one week of being placed in an eye.

It may be desirable to provide a relatively constant rate of release of the prostamide from the implant over the life of the implant. For example, it may be desirable for the prostamide to be released in amounts from about 0.01 .mu.g to about 2 .mu.g per day for the life of the implant. However, the release rate may change to either increase or decrease depending on the formulation of the biodegradable polymer matrix. In addition, the release profile of the prostamide may include one or more linear portions and/or one or more non-linear portions. Preferably, the release rate is greater than zero once the implant has begun to degrade or erode.

The implants may be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic component, including the prostamide, may be distributed in a non-homogenous pattern in the matrix. For example, the implant may include a portion that has a greater concentration of the prostamide relative to a second portion of the implant.

The intraocular implants disclosed herein may have a size of between about 5 .mu.m and about 10 mm, or between about 10 .mu.m and about 1 mm for administration with a needle, greater than 1 mm, or greater than 2 mm, such as 3 mm or up to 10 mm, for administration by surgical implantation. For needle-injected implants, the implants may have any appropriate length so long as the diameter of the implant permits the implant to move through a needle. For example, implants having a length of about 6 mm to about 7 mm have been injected into an eye. The implants administered by way of a needle should have a diameter that is less than the inner diameter of the needle. In certain implants, the diameter is less than about 500 .mu.m. The vitreous chamber in humans is able to accommodate relatively large implants of varying geometries, having lengths of, for example, 1 to 10 mm. The implant may be a cylindrical pellet (e.g., rod) with dimensions of about 2 mm.times.0.75 mm diameter. Or the implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 .mu.g, more preferably about 500-1000 .mu.g. For example, an implant may be about 500 .mu.g, or about 1000.mu.g. For non-human individuals, the dimensions and total weight of the implant(s) may be larger or smaller, depending on the type of individual. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Thus, implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be, rapidly washed out of the eye.

The implants may be of any geometry including fibers, sheets, films, microspheres, spheres, circular discs, plaques and the like. The upper limit for the implant size will be determined by factors such as toleration for the implant, size limitations on insertion, ease of handling, etc. Where sheets or films are employed, the sheets or films will be in the range of at least about 0.5 mm.times.0.5 mm, usually about 3-10 mm.times.5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of about 0.5 .mu.m to 4 mm in diameter, with comparable volumes for other shaped particles.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

Preferably the implant is sized to fit the anatomy of the iridocorneal angle of the eye.

The proportions of the prostamide, polymer, and any other modifiers may be empirically determined by formulating several implants with varying proportions. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the drug concentration is after release is less than 5% of saturation. The mixture is maintained at 37 .degree. C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

In addition to the prostamide included in the intraocular implants disclosed herein, the intraocular implants may also include one or more additional ophthalmically acceptable therapeutic agents as described in U.S. patent application Ser. No. 10/837,260.

For example, one implant may comprise a combination of bimatoprost and a beta-adrenergic receptor antagonist. More specifically, the implant may comprise a combination of bimatoprost and Timolol™. Or, an implant may comprise a combination of bimatoprost and a carbonic anyhdrase inhibitor. For example, the implant may comprise a combination of bimatoprost and dorzolamide (Trusopt™.).

One implant may comprise a combination of bimatoprost and latanoprost. Another implant may comprise a combination of bimatoprost and travoprost.

In addition to the therapeutic component, as described in U.S. patent application Ser. No. 10/837,260, the intraocular implants disclosed herein may include effective amounts of buffering agents, preservatives and the like.

In at least one of the present implants, a benzylalkonium chloride preservative is provided in the implant, such as when the prostamide consists essentially of bimatoprost.

Additionally, release modulators such as those described in U.S. Pat. No. 5,869,079 may be included in the implants. The amount of release modulator employed will be dependent on the desired release profile, the activity of the modulator, and on the release profile of the prostamide in the absence of modulator. Electrolytes such as sodium chloride and potassium chloride may also be included in the implant. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

In certain implants, an implant comprising bimatoprost and a biodegradable polymer matrix is able to release or deliver an amount of bimatoprost between about 0.1 mg to about 0.5 mg for about 3-6 months after implantation into the eye. The implant may be configured as a rod or a wafer. A rod-shaped implant may be derived from filaments extruded from a 720 .mu.m nozzle and cut into 1 mg size. A wafer-shaped implant may be a circular disc having a diameter of about 2.5 mm, a thickness of about 0.127 mm, and a weight of about 1 mg.

Various techniques may be employed to produce the implants described herein, as described in U.S. patent application Ser. No. 10/837,260, incorporated entirely by reference.

The present implants are configured to release an amount of prostamide effective to treat an ocular condition, such as by reducing at least one symptom of the ocular condition. More specifically, the implants may be used in a method to treat glaucoma, such as open angle glaucoma, ocular hypertension, chronic angle-closure glaucoma, with patent iridotomy, psuedoexfoliative glaucoma, and pigmentary glaucoma. By implanting the prostamide-containing implants into the vitreous of an eye, it is believed that the prostamide is effective to enhance aqueous humour flow thereby reducing intraocular pressure.

The implants disclosed herein may also be configured to release the prostamide or additional therapeutic agents, as described above, which to prevent or treat diseases or conditions, such as described in U.S. patent application Ser. No. 10/837,260.

In one embodiment, an implant, such as the implants disclosed herein, is administered to a posterior segment of an eye of a human or animal patient, and preferably, a living human or animal. In at least one embodiment, an implant is administered without accessing the subretinal space of the eye. For example, a method of treating a patient may include placing the implant directly into the posterior chamber of the eye. In other embodiments, a method of treating a patient may comprise administering an implant to the patient by at least one of intravitreal injection, subconjuctival injection, sub-tenon injections, retrobulbar injection, and suprachoroidal injection.

In at least one embodiment, a method of reducing intraocular pressure in an eye of a patient comprises administering one or more implants containing a prostamide, as disclosed herein, to a patient by at least one of intravitreal injection, subconjuctival injection, sub-tenon injection, retrobulbar injection, and suprachoroidal injection. A syringe apparatus including an appropriately sized needle, for example, a 22-30 gauge needle, such as a 22 gauge needle, a 27 gauge needle, a 28 gauge needle, or a 30 gauge needle, can be effectively used to inject the composition with the posterior segment of an eye of a human or animal. Repeat injections are often not necessary due to the extended release of the prostamide from the implants.

In addition, for dual therapy approaches to treating an ocular condition, the method may include one or more additional steps of administering additional therapeutic agents to the eye, such as by topically administering compositions containing timolol, dorzolamide, and iatoprost, among others.

In certain implants, the implant comprises a therapeutic component which consists essentially of bimatoprost, salts thereof, and mixtures thereof, and a biodegradable polymer matrix. The biodegradable polymer matrix may consist essentially of PLA, PLGA, or a combination thereof. When placed in the eye, the implant releases about 40% to about 60% of the bimatoprost to provide a loading dose of the bimatoprost within about one day after placement in the eye. Subsequently, the implant releases about 1% to about 2% of the bimatoprost per day to provide a sustained therapeutic effect. Such implants may be effective in reducing and maintaining a reduced intraocular pressure, such as below about 15 mm Hg for several months, and potentially for one or two years.

Other implants disclosed herein may be configured such that the amount of the prostamide that is released from the implant within two days of being placed in the eye is less than about 95% of the total amount of the prostamide in the implant. In certain implants, 95% of the prostamide is not released until after about one week of being placed in an eye. In certain implants, about 50% of the prostamide is released within about one day of placement in the eye, and about 2% is released for about 1 month after being placed in the eye. In other implants, about 50% of the prostamide is released within about one day of placement in the eye, and about 1% is released for about 2 months after being placed in the eye.

The following examples are intended to illustrate the present invention.

EXAMPLE 1

Intracameral Bimatoprost Implant with High Initial Release Rate

Figure 8:
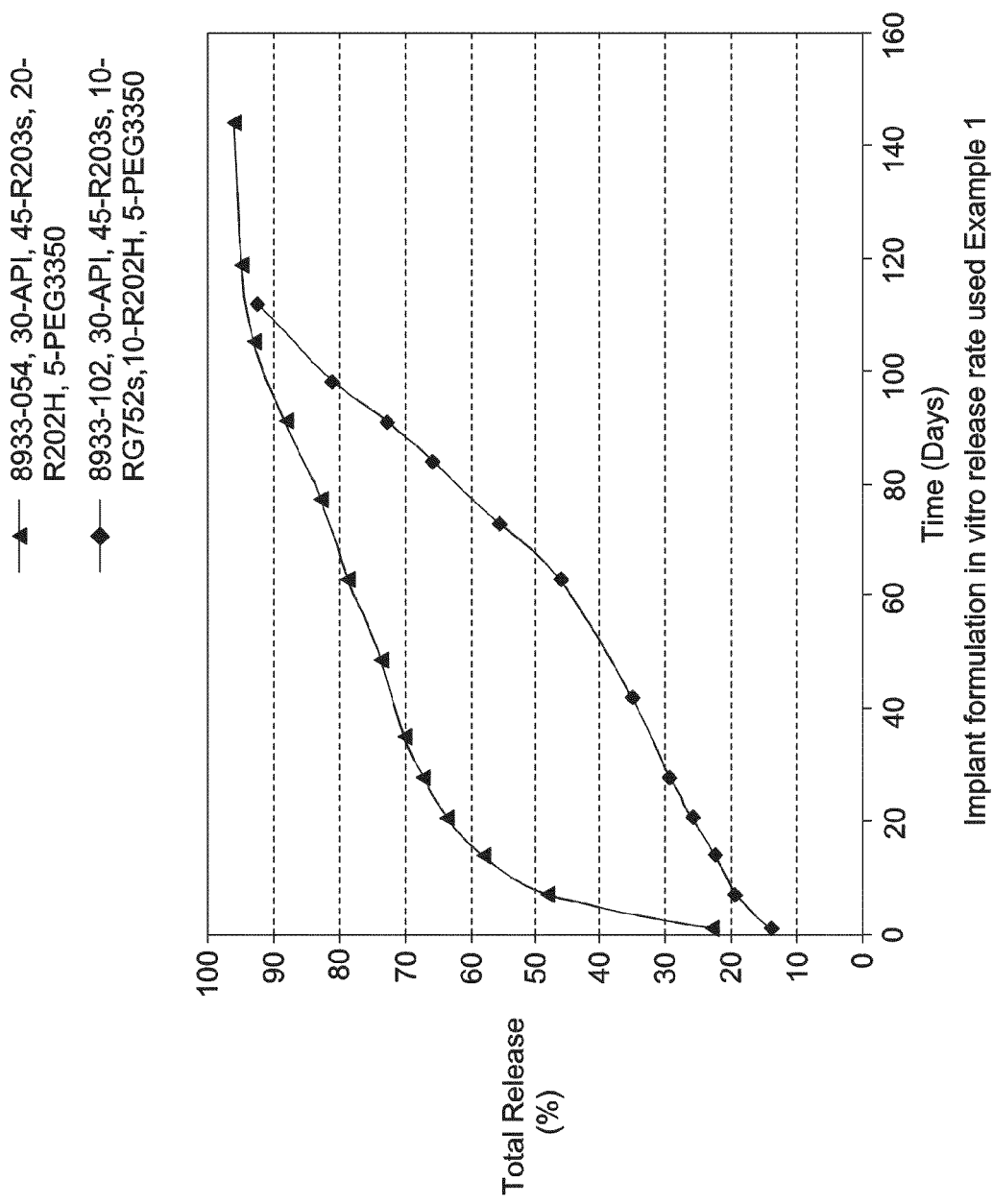
FIG. 8 shows the in vitro release rate of the Implant formulation used in Example 1 (arrow).

A bimatoprost implant comprising Bimatoprost 30%, R203S 45%, R202H 20%, PEG 3350 5% was manufactured with a total implant weight of 900 mg (drug load 270 ug). The in vitro release rates of this implant are shown in FIG. 8. This implant releases ~70% over first 30 days. An implant with a 270 ug drug load would release 189 ug over first 30 days or 6.3 ug per day. The remainder of the implant (81ug) is released over the next 4 months (i.e. 675 ng per day).

Figure 4:
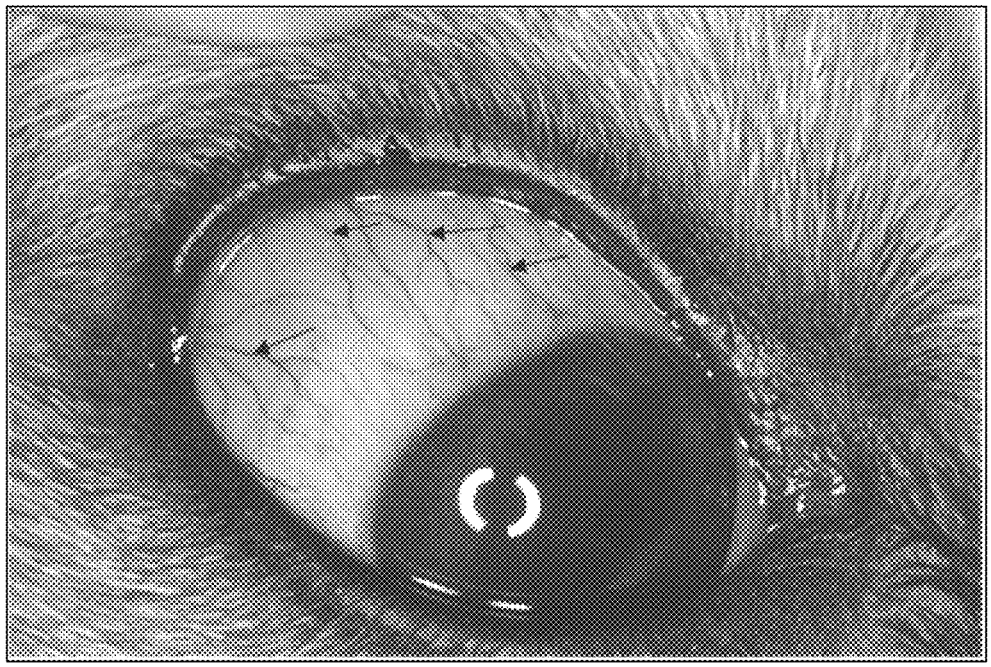
FIG. 4 is a photograph showing the outflow vessels that are dilated as a result of treatment of a dog with the high-release bimatoprost intracameral implant of Example 1.
Figure 5:
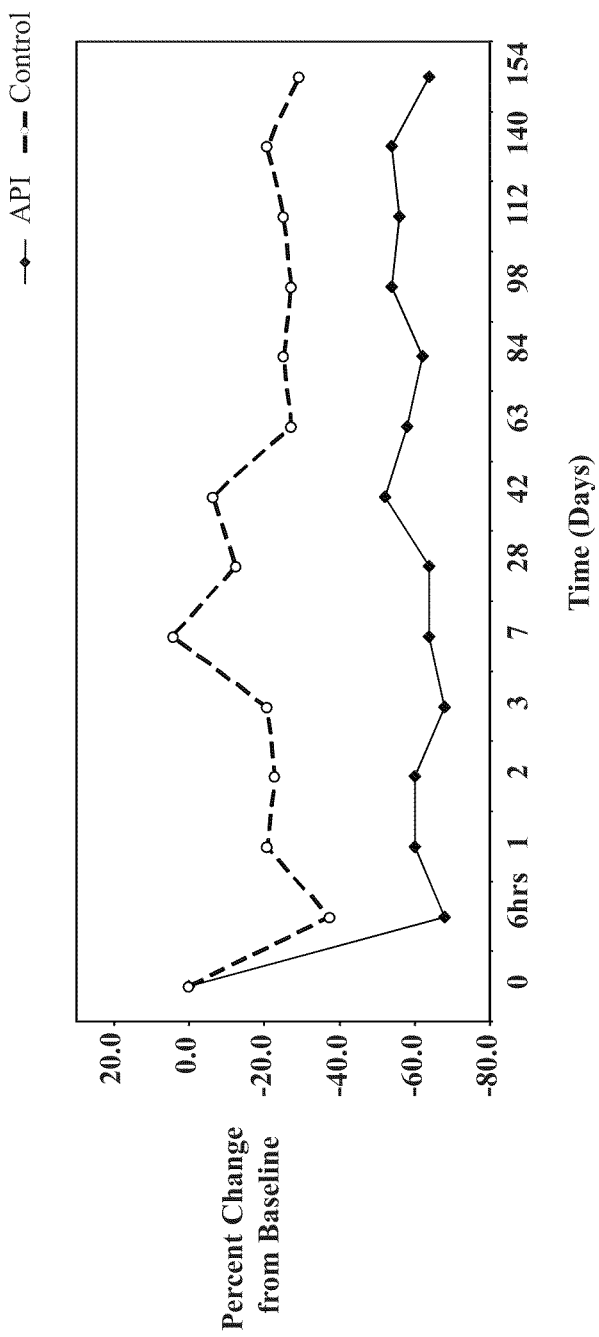
FIG. 5 shows the IOP of a dog treated with the high-release bimatoprost intracameral implant described in Example 1 was reduced to approximately −60% from baseline and such reduction was sustained for at least 5 months.

A normal beagle dog was given general anesthesia and a 3 mm wide keratome knife was used to enter the anterior chamber of the right eye. The intracameral bimatoprost implant was placed in the anterior chamber and it settled out in the inferior angle within 24 hours. As shown in FIG. 5, the IOP was reduced to approximately −60% from baseline and this was sustained for at least 5 months (See FIG. 5). As shown in FIG. 4, the episcleral vessels are dilated.

EXAMPLE 2

Intracameral Bimatoprost Implant with Slow Initial Release Rate

Figure 9:
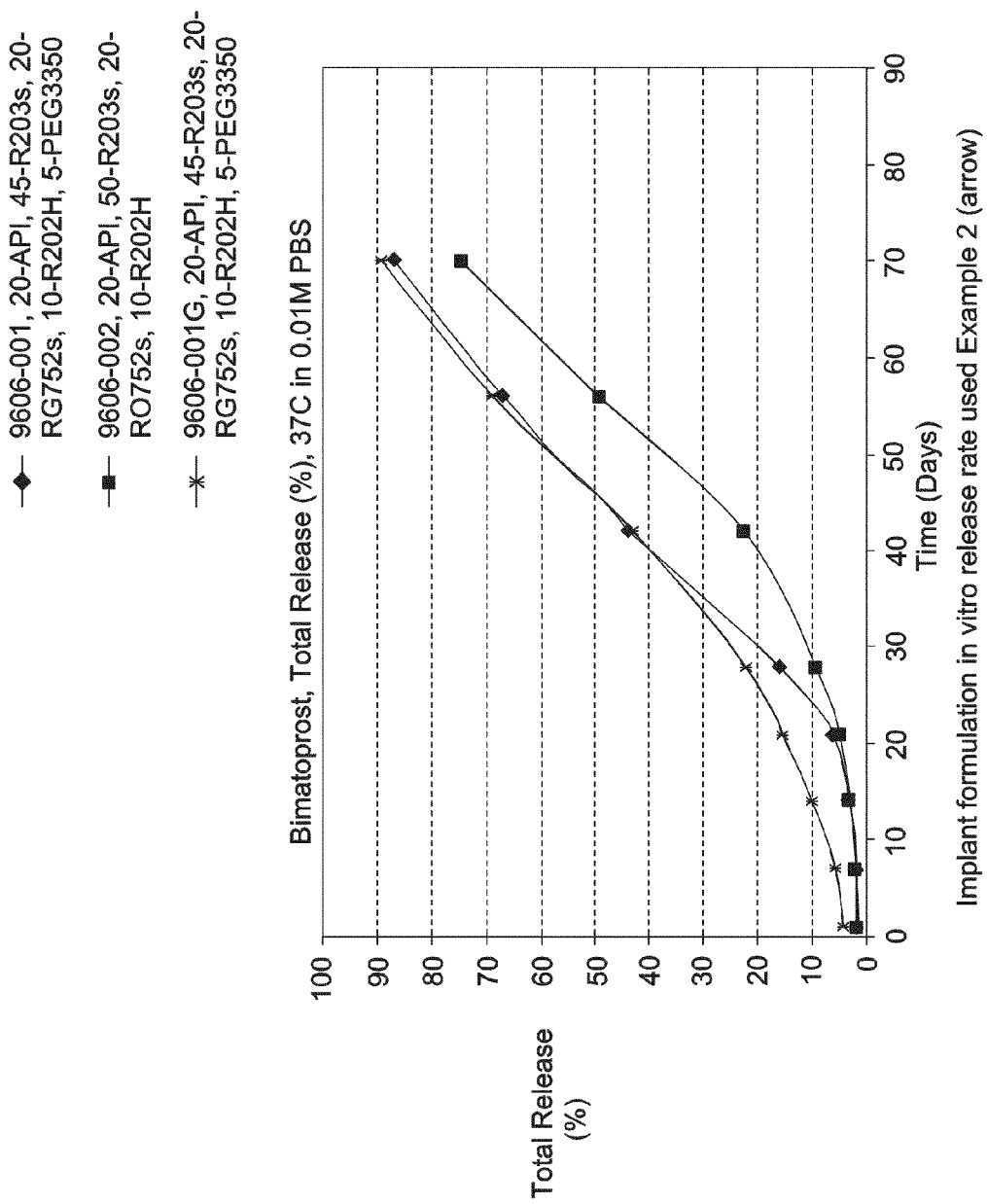
FIG. 9 shows the in vitro release rate of the Implant formulation used in Example 2 (arrow).

A bimatoprost implant comprising Bimatoprost 20%, R203S 45%, R202H 10%, RG752S 20%, PEG 3350 5% was manufactured with a total implant weight of 300 ug or 600 ug (drug loads of 60 or 120 ug, respectively). The in vitro release rates of this implant are shown in FIG. 9. The implant releases ~15% of the drug load over the first month. An implant with a 60 ug drug load would release 9 ug over first 30 days or 300 ng per day, thereafter, it releases ~50 ug over 60 days or ~700 ng/day. Like Example 1, it was found that the episcleral vessels were dilated.

EXAMPLE 3

The following experiment was carried out by inserting the implants described below in six Beagle dogs:

Implant Formulations:

2 mm Bimatoprost implant in applicator (20% Bimatoprost, 45% R203s, 20% RG752s, 10% R202H, 5% PEG-3350)

2 mm, Placebo implant in applicator (56.25% R203s, 25% RG752s, 12.25% R202H, 6.25% PEG-3350)

Dog 1,2,3: API implant intracameral OD (one 2 mm implant), OS placebo implant

Dog 4,5,6: API implant intracameral OD (two 2 mm implants), OS placebo implant

| Dog ID | Implant Weight (mg) | Drug Dose (20% load, ug) |
| --- | --- | --- |
| CYJ AUS | 0.317 | 63.4 |
| CYJ AYE | 0.326 | 65.2 |
| CYJ AUR | 0.315 | 63.0 |
| CYJ AUG | 0.302 0.331 | 126.6 |
| CYJ BAV | 0.298 0.329 | 125.4 |
| CYJ BBY | 0.306 0.327 | 126.6 |

Surgical Procedure: Implants were loaded in a customized applicator with a 25G UTW needle. Under general anesthesia, normal beagle dogs had the implant inserted in the anterior chamber through clear cornea and the wound was self-sealing. The applicator is described in Published United States Patent Application 20080033351 incorporated entirely by reference.

Figure 6:
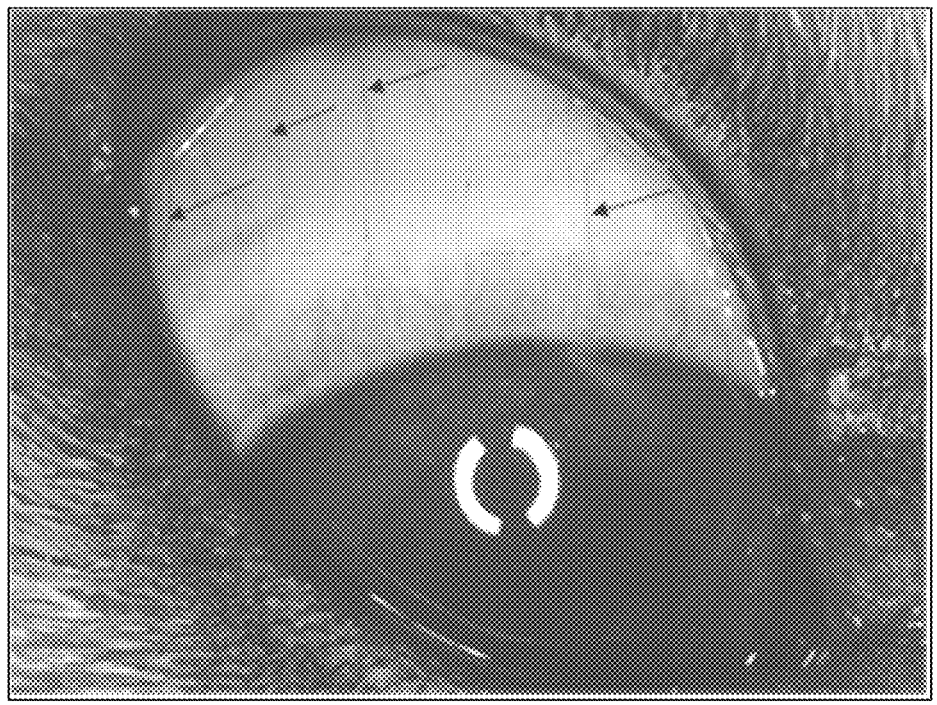
FIG. 6 is a photograph showing the outflow vessels that are dilated as a result of treatment of a dog with the low-release bimatoprost intracameral implant of Example 2.
Figure 7:
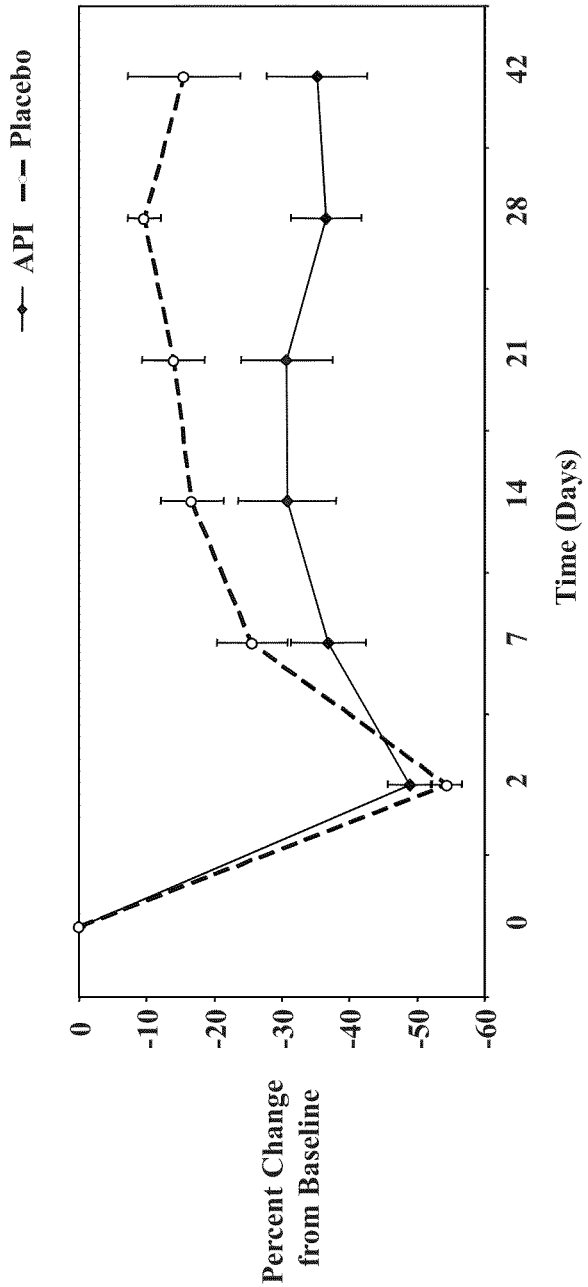
FIG. 7 shows the IOP of a dog treated with the low-release bimatoprost intracameral implant described in Example 2 was reduced to approximately −40% from baseline and such reduction was sustained for at least 42 days.
Figure 10:
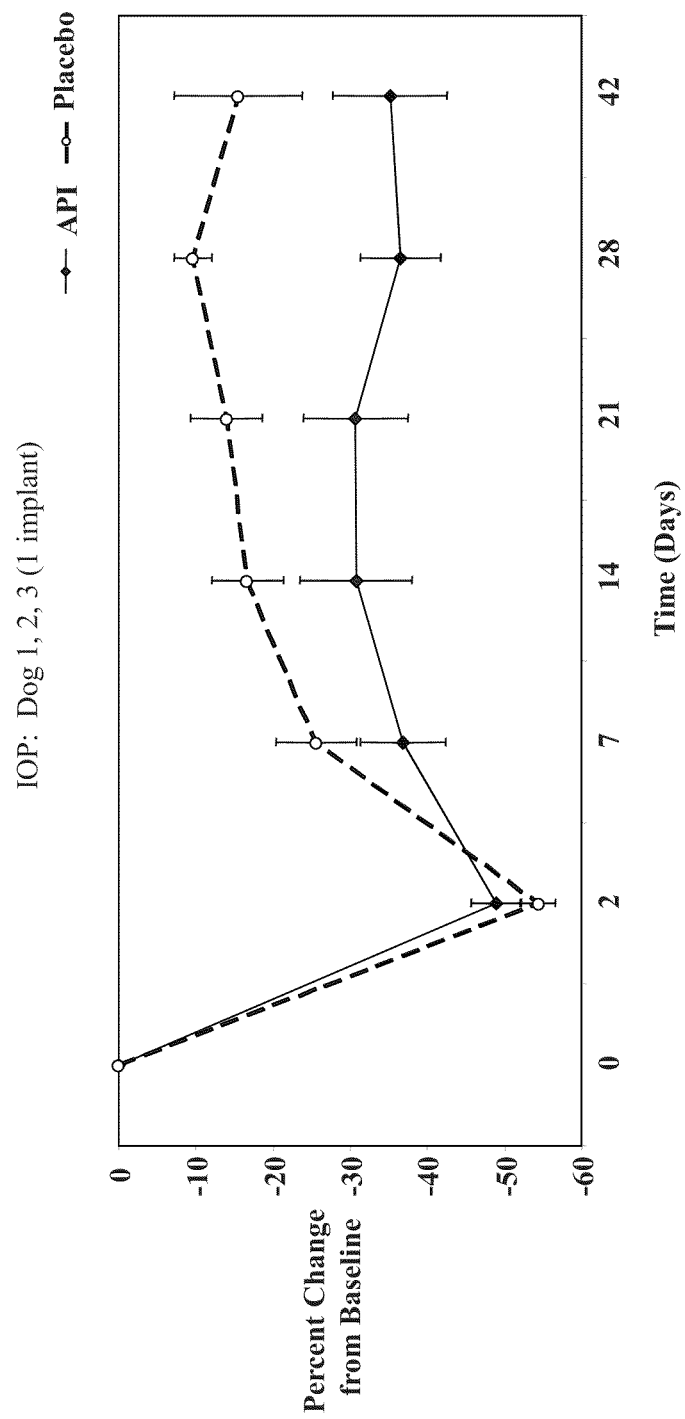
FIG. 10 shows the IOP is lowered in a dog treated with a single bimatoprost implant according to Example 3.
Figure 11:
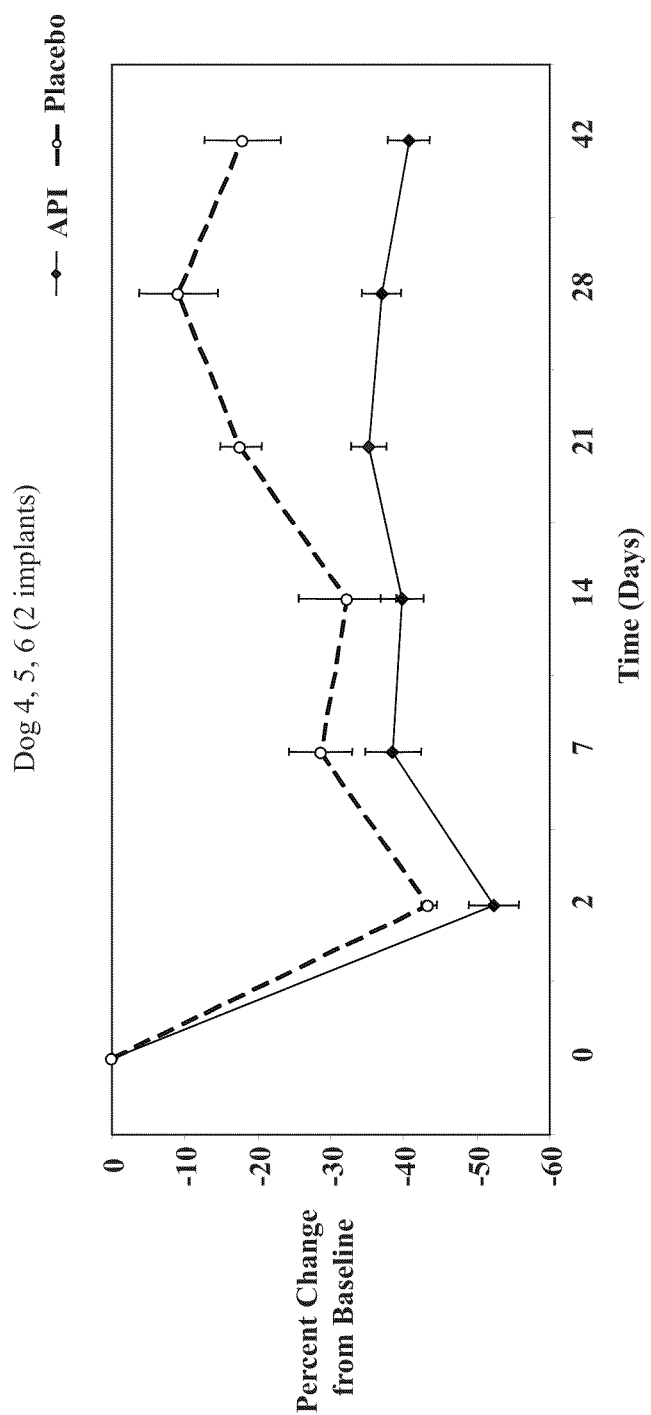
FIG. 11 shows the IOP is lowered in a dog treated with two bimatoprost implants according to Example 3.

The experimental results are reported in FIGS. 10 and 11. There was a reduction of IOP up to 40% in dogs treated with intracameral bimatoprost implants with a greater mean reduction at most time points in animals with 2 implants. As shown in FIG. 6, the dilation of the episcleral outflow vessels was observed in the animals with the active implants in this Example 3, but said vessels were less dilated compared with the test animal treated with the faster drug releasing implant used in Example 1.

EXAMPLE 4

Pre-filled applicators were used to administer the implant to 4 dogs per dose. (It was noted that the Bimato IC DDS, which is disclosed in Published US Patent Application 20080033351, releases only the amide. In FIGS. 12 and 13, PK data with different doses of the implant is shown. It is noted that there is a dose response, and the predominant species, especially in the ICB, is the amide.)

The present invention is not to be limited in scope by the exemplified embodiments, which are only intended as illustrations of specific aspects of the invention. Various modifications of the invention, in addition to those disclosed herein, will be apparent to those skilled in the art by a careful reading of the specification, including the claims, as originally filed. In particular, while the present invention, as disclosed above discloses a prostamide as the active pharmaceutical ingredient or API, one may utilize a prostaglandin (or a drug that is effective to lower the elevated IOP of a patient) or a prodrug thereof as the API. The prostaglandin or prodrug thereof of the implant may include one or more types of prostaglandin or prodrug thereofs. In these implants, the prostaglandin or prodrug thereof comprises a compound having the formula (I).

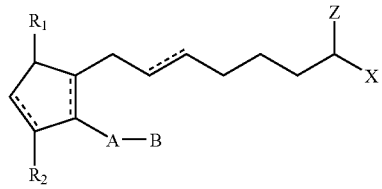

wherein the dashed bonds represent a single or double bond which can be in the cis or trans configuration, A is an alkylene or alkenylene radical having from two to six carbon atoms, which radical may be interrupted by one or more oxide radicals and substituted with one or more hydroxy, oxo, alkyloxy or alkylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is —(OR$^4$), wherein R.$^4$ is independently selected from the group consisting of hydrogen and a lower alkyl radical having from one to six carbon atoms, Z is =O; one of $R_1$ and $R_2$ is =O, —OH or a —O(CO)$R_6$ group, and the other one is —OH or —O(CO)$R_6$, or $R_1$ is =O and $R_2$ is H; wherein $R_6$ is a saturated or unsaturated acyclic hydrocarbon group having from 1 to about 20 carbon atoms, or —(CH$_2$)m$R_7$ wherein m is 0-10, and $R_7$ is cycloalkyl radical, having from three to seven carbon atoms, or a hydrocarbyl aryl or heteroaryl, as defined above.

Preferably, the prostaglandin or prodrug thereof has the following formula (II)

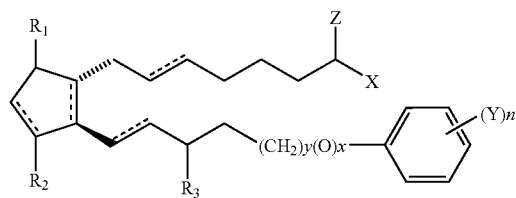

wherein y is 0 or 1, x is 0 or 1 and x+y are not both 1, Y is a radical selected from the group consisting of alkyl, halo, nitro, amino, thiol, hydroxy, alkyloxy, alkylcarboxy and halo substituted alkyl, wherein said alkyl radical comprises from one to six carbon atoms, n is 0 or an integer of from 1 to 3 and $R_3$ is =O, —OH or —O(CO)$R_6$ and hatched lines indicate the .alpha. configuration and solid triangles indicate the .beta. configuration.

In at least one type of intraocular implant, the prostaglandin prodrug comprises a compound wherein $R_1$, $R_2$ and $R_3$ are OH, y is 1, x is 0, n is 0 and X is (OC$_3$H$_7$),e.g. cyclopentane hepten-5-oic acid-cis-2-(3α.-hydroxy-5-phenylpentyl)-3,5-dihydroxy, isopropyl ester [1$_α$.,2$_β$.,3$_α$.,5$_α$.], i.e. latanoprost.

In at least other one type of intraocular implant, the prostaglandin prodrug comprises a compound wherein $R_1$, $R_2$ and $R_3$ are OH, y is 0, x is 1, n is 1, Y is CF$_3$ and X is (OC$_3$H$_7$),e.g. cyclopentane hepten-5-oic acid-cis-2-(3α.-hydroxy-5-phenylpentyl)-3,5-dihydroxy, isopropyl ester [1$_α$.,2$_β$.,3$_α$.,5$_α$.], i.e. travoprost.

Alternatively, the prostaglandin may be unoprostone. Thus, the implant may comprise a therapeutic component which comprises, consists essentially of, or consists of latanoprost, or travoprost or unoprostone.

It is intended that all such modifications will fall within the scope of the appended claims.

What is claimed is:

1. A method of treating an ocular condition, comprising the step of placing a biodegradable intraocular implant in an eye of the patient in need of said treatment, said implant comprising a therapeutic component associated with a biodegradable polymer matrix that releases an amount of the therapeutic component effective to reduce a symptom of the ocular condition of the eye, wherein said ocular condition is elevated intraocular pressure (IOP), wherein the therapeutic component consists of a postamide, and wherein said implant is placed in the anterior chamber of the eye.

2. The method of claim 1 wherein said prostamide is a compound having the formula (I)

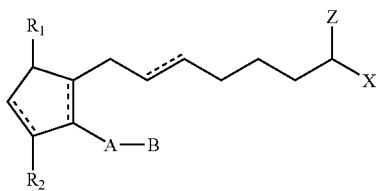

wherein the dashed bonds represent a single or double bond which can be in the cis or trans configuration, A is an alkylene or alkenylene radical having from two to six carbon atoms, which radical may be interrupted by one or more oxide radicals and substituted with one or more hydroxy, oxo, alkyloxy or akylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is —N($R^4$)$_2$ wherein $R^4$ is independently selected from the group consisting of hydrogen and a lower alkyl radical having from one to six carbon atoms; Z is =O; one of $R_1$ and $R_2$ is =O, —OH or a —O(CO)$R_6$ group, and the other one is —OH or —O(CO)$R_6$, or $R_1$ is =O and $R_2$ is H; wherein $R_6$ is a saturated or unsaturated acyclic hydrocarbon group having from 1 to about 20 carbon atoms, or —(CH$_2$)mR$_7$ wherein m is 0-10, and $R_7$ is cycloalkyl radical, having from three to seven carbon atoms, or a hydrocarbyl aryl or heteroaryl radical, as defined above.

3. The method of claim 2 wherein the prostamide has the following formula (II)

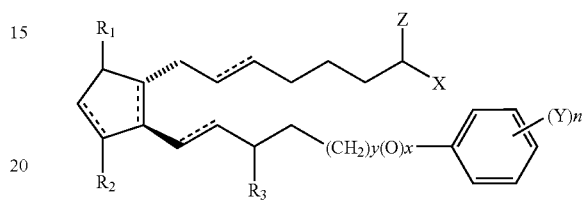

wherein y is 0 or 1, x is 0 or 1 and x+y are not both 1, Y is a radical selected from the group consisting of alkyl, halo, nitro, amino, thiol, hydroxy, alkyloxy, alkylcarboxy and halo substituted alkyl, wherein said alkyl radical comprises from one to six carbon atoms, n is 0 or an integer of from 1 to 3 and $R_3$ is =O, —OH or —O(CO)$R_6$ and hatched lines indicate the a configuration and solid triangles indicate the β configuration.

4. The method of claim 1, wherein the amount of prostamide is released into the eye for a period of time greater than about one week after the implant is placed in the eye.

5. The method of claim 1, wherein the prostamide is bimatoprost.

* * * * *